United States Patent
Doshi et al.

(10) Patent No.: US 12,178,904 B2
(45) Date of Patent: Dec. 31, 2024

(54) CONTACT LENSES INCLUDING MEDICAMENTS AND METHODS OF MAKING AND USING SAME INCLUDING STABILIZERS OF LABILE COMPONENTS SUCH AS DRUGS

(71) Applicant: Mediprint Ophthalmics Inc., San Diego, CA (US)

(72) Inventors: Praful Doshi, San Diego, CA (US); Brandon Huang, San Diego, CA (US); Stephen Halbe, San Diego, CA (US); Neil Patodia, San Diego, CA (US); Pavanasam Natarajan Balasubramanian, San Diego, CA (US)

( * ) Notice: Subject to any disclaimer, the term of this patent is extended or adjusted under 35 U.S.C. 154(b) by 0 days.

(21) Appl. No.: 18/606,551

(22) Filed: Mar. 15, 2024

(65) Prior Publication Data

US 2024/0285522 A1 Aug. 29, 2024

Related U.S. Application Data

(63) Continuation of application No. PCT/US2023/070203, filed on Jul. 14, 2023.

(60) Provisional application No. 63/368,515, filed on Jul. 15, 2022.

(51) Int. Cl.
| | |
|---|---|
| A61L 27/54 | (2006.01) |
| A61F 9/00 | (2006.01) |
| A61K 9/00 | (2006.01) |
| A61K 9/107 | (2006.01) |
| A61K 31/00 | (2006.01) |
| A61K 31/46 | (2006.01) |
| A61K 31/5575 | (2006.01) |
| A61K 47/40 | (2006.01) |

(52) U.S. Cl.
CPC .......... *A61K 9/0051* (2013.01); *A61F 9/0017* (2013.01); *A61K 9/1075* (2013.01); *A61K 31/46* (2013.01); *A61K 31/5575* (2013.01); *A61K 31/658* (2023.05); *A61K 47/40* (2013.01)

(58) Field of Classification Search
None
See application file for complete search history.

(56) References Cited

U.S. PATENT DOCUMENTS

| | | |
|---|---|---|
| 3,618,604 A | 11/1971 | Ness |
| 3,786,812 A | 1/1974 | Neefe |
| 3,828,777 A | 8/1974 | Ness |
| 6,294,553 B1 | 9/2001 | Gil et al. |
| 6,887,858 B1 | 5/2005 | Yerxa |
| 7,638,137 B2 | 12/2009 | Chauhan et al. |
| 9,421,199 B2 | 8/2016 | Ostrow et al. |
| 9,539,262 B2 | 1/2017 | Khopade et al. |
| 9,931,296 B2 | 4/2018 | Doshi |
| 10,413,506 B2 | 9/2019 | Doshi |
| 10,463,677 B2 | 11/2019 | Esaki et al. |
| 10,617,559 B2 | 4/2020 | Yang et al. |
| 10,940,145 B2 | 3/2021 | Ostrow et al. |
| 11,173,064 B2 | 11/2021 | Yang et al. |
| 2009/0004244 A1 | 1/2009 | Orilla et al. |
| 2009/0004245 A1 | 1/2009 | Orilla et al. |
| 2012/0021013 A1 | 1/2012 | Esaki et al. |
| 2015/0056294 A1 | 2/2015 | Kaplan et al. |
| 2018/0036974 A1 | 2/2018 | Han et al. |
| 2020/0297714 A1 | 9/2020 | Ostrow et al. |
| 2021/0317385 A1 | 10/2021 | MacDonald et al. |
| 2021/0346285 A1 | 11/2021 | Doshi |
| 2022/0192975 A1 | 6/2022 | Yang |

FOREIGN PATENT DOCUMENTS

| | | |
|---|---|---|
| EP | 1681059 | 8/1974 |
| WO | WO 2024/015959 | 1/2024 |

OTHER PUBLICATIONS

Kirchhoff et al., Analysis of atropine, its degradation products and related substances of natural origin by means of reverse-phase high-performance liquid chromatography, J. Chromatography, A 1046 (2004) 115-120.
Rodriquez-Alder et al., New prostaglandin analog formation for glaucoma treatment containing cyclodextrins for improved stability, solubility and ocular tolerance, European Journal of Pharmaceutics and Biopharmaceuticals, vol. 95, Part B (2015) 203-214.
PCT Search Report and Written Opinion for PCT/US23/70203 (WO 2024/015959), Nov. 21, 2023.

*Primary Examiner* — David J Blanchard
*Assistant Examiner* — Daniel F Coughlin
(74) *Attorney, Agent, or Firm* — David R. Preston

(57) ABSTRACT

The present invention recognizes that medical devices, such as but not limited to contact lenses, can be made having at least one coating made at least in part using printing technologies to provide drug storage and drug release structures, notably for hydrophobic drugs and that such hydrophobic drugs can be stabilized as to hydrolysis, heat, and a combination thereof. A first aspect of the present invention includes a packaged medical device that includes at least one drug delivery contact lens. A second aspect of the present invention includes a drug delivery contact lens. A third aspect of the present invention includes a method of making a drug delivery contact lens. A fourth aspect of the present invention includes an ink. A fifth aspect of the present invention includes a method of using a drug delivery contact lens to treat or prevent a disease, disorder, or condition of the eye.

90 Claims, 8 Drawing Sheets

CONTACT LENSES INCLUDING MEDICAMENTS AND METHODS OF MAKING AND USING SAME INCLUDING STABILIZERS OF LABILE COMPONENTS SUCH AS DRUGS

PRIORITY STATEMENT

The present application is a Continuation of PCT Application Number PCT/US2023/070203, filed Jul. 14, 2023, which
claims benefit of priority to U.S. Provisional Application No. 63/368,515, filed Jul. 15, 2022;
each of which is incorporated by reference in its entirety herein.

TECHNICAL FIELD

The present invention generally relates generally to the fields of medical devices, including but not limited to contact lenses, that include a medicament or drug in a coating layer and methods of making and using such medical devices. The coating layer is preferably made at least in part using printing, preferably but not limited to digital printing.

BACKGROUND

Medical devices that include a medicament have been known. Examples include contact lenses and stents for the treatment or prevention of a variety of diseases, disorders or conditions, such as contact lenses for the treatment of glaucoma and stents for the treatment or prevention of restinosis. Existing medical devices that include medicaments are traditionally made using relatively simple drug coating or drug impregnation technologies that do not allow the modulated release of the medicament from the coating. The present invention addresses these limitations and provides additional benefits as well.

A variety of medical devices, particularly contact lenses, that include a medicament have been described. For example, U.S. Pat. No. 7,638,137B2 to Chuahan et al. describes drug delivery systems through dispersion of transparently encapsulated drugs within the lens. However, such dispersion inside the lens could alter the physical properties of the polymeric lens materials. Also, while encapsulated drugs may be visually transparent in certain instances, the may interfere with the optical properties of the lens. Also, drugs inside the lens may be released from either or both the anterior and posterior surfaces of the lens and thus not providing the desired dosage of a drug to the cornea or other areas of an eye structure and surrounding tissues. This document also provides a survey of the literature relating to issues relating to drug release.

U.S. published Patent Application No. 2009/07504245A1 to Orilla et al. describe the masking of a color of a drug by applying a color layer on top of the drug. This document does not relate to the controlling the drug release rate from the lens.

Also, U.S. published Patent Application No. 2009/0004244 to Burke et al. describes deposing a drug in an iris simulated pattern to provide a cosmetic appearance of a lens for drug delivery. This document does not relate to how drug release rate can be controlled.

In addition, U.S. Pat. No. 6,887,858 to Yerxa describes formulations for the treatment of dry eye diseases. The document is not related to drug release from a medical device such as a contact lens.

Furthermore, U.S. Pat. No. 6,294,553 to Gil et al. describes a drug for ocular surface pain. Gil et al. does not, however relate to controlled drug delivery rate.

U.S. Pat. No. 3,786,812 to Neefe describes the use of contact lenses for drug delivery. This document, however, does not relate to achieving desired release rate of a drug from a lens.

Also, U.S. Pat. Nos. 3,618,604 and 3,828,777 describe polymeric plastics in which a drug is held to provide controlled drug release rate. The documents, however, do not relate to the ability to adjust drug release rate.

In addition, U.S. Pat. No. 10,463,677 generally relates to stabilization of latanoprost by cyclodextrin.

Also, Published US Patent Application No. 2012/0021013 generally relates to stabilization of latanoprost by cyclodextrin.

Furthermore, Rodriguez-Aller et al. "New Prostaglandin analog formations for glaucoma treatment containing cyclodextrins for improved stability, solubility and ocular tolerance" European Journal of Pharmaceutics and Biopharmaceutics, Volume 95, Part B, Pg 203-214 (2015) (Abstract only) https://www.sciencedirect.com/science/article/abs/pii/S093964111500212X?via%3Dihub.

In addition, U.S. Pat. No. 9,539,262 generally relates to prostaglandin derivates such as latanoprost formulated with polyethylene glycol hyroxystearate having decreased absorption that was not addressed by addition of oil.

Also, EP 1681059 generally relates to the effects of different formulation conditions such as pH on the degradation of latanoprost.

Furthermore, U.S. Pat. Nos. 9,931,296 and 10,413,506, all to Doshi generally relate to drug release contact lenses.

In addition, U.S. Pat. Nos. 10,617,559, 11,173,064, and US Published Application No. 2002/0192975, all to Yang generally relate to drug release contact lenses.

SUMMARY

Figure 1:
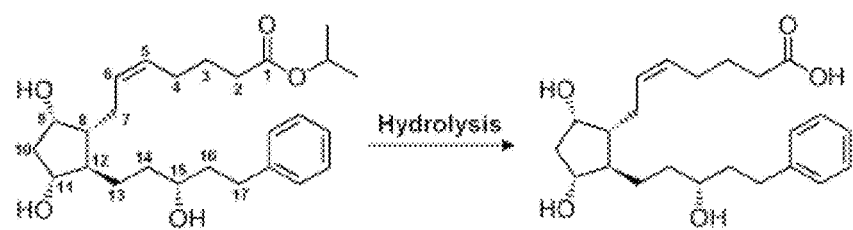
FIG. 1 generally depicts a proposed mechanism of Latanoprost Hydrolysis to Latanoprost Free Acid. The isopropyl ester on carbon 1 easily hydrolyzes at ambient room temperature, producing Latanoprost free acid.

The present invention recognizes that medical devices, such as but not limited to contact lenses, can be made having at least one coating made at least in part using printing technologies to provide drug storage and drug release structures, notably for hydrophobic drugs and that such hydrophobic drugs can be stabilized as to hydrolysis, heat, and a combination thereof.

A first aspect of the present invention includes a medical device that incorporates at least one drug in at least one coating, in general.

A second aspect of the present invention includes a method of making a medical device that incorporates at least one drug in at least one coating, in general.

A third aspect of the present invention includes a method of using a medical device of the present invention to treat or prevent a disease, disorder or condition, in general.

A fourth aspect of the present invention includes a packaged medical device that includes at least one drug delivery contact lens.

A fifth aspect of the present invention includes a drug delivery contact lens.

A sixth aspect of the present invention includes a method of making a drug delivery contact lens.

A seventh aspect of the present invention includes an ink.

An eight aspect of the present invention includes a method of using a drug delivery contact lens to treat or prevent a disease, disorder, or condition of the eye.

DETAILED DESCRIPTION OF THE INVENTION

Definitions

Unless defined otherwise, all technical and scientific terms used herein have the same meaning as commonly understood by one of ordinary skill in the art to which this invention belongs. Generally, the nomenclature used herein and the laboratory procedures well known and commonly employed in the art. Conventional methods are used for these procedures, such as those provided in the art and various general references such as U.S. Pat. Nos. 5,160,463; 5,271,874; 5,018,849; 5,034,166; 5,414,477; 6,315,410; 6,899,426B2; 7,638,137B2; US Published Patent Application US2009/0062381A1; Day et al., Current Optometric Information and Terminology, Third Edition, American Optometric Association (1980); Howley's Condensed Chemical Dictionary (1981); Federation of Societies for Coatings Technology; and "Contact Lenses for Drug Delivery: Achieving Sustained Release with Novel Systems," Alvarez Lorenzo et. al. American Journal of Drug Delivery, (2006) 4 (3) (3) (5). Where a term is provided in the singular, the inventors also contemplate the plural of that term. The nomenclature used herein and the laboratory procedures described below are those well-known and commonly employed in the art. As employed throughout the disclosure, the following terms, unless otherwise indicated, shall be understood to have the following meanings:

"Directly" refers to direct causation of a process that does not require intermediate steps.

"Indirectly" refers to indirect causation that requires intermediate steps.

"Digitally Encoded Image" or "Digital Image" refers to an image that has been created or stored in a digital format. A digitally encoded image can be made using methods known in the art, such as artistic renditions or scanning or otherwise translating an image. A digitally encoded image can be stored on appropriate storage medium, such as magnetic medium or polymers such as cyclo-olefin copolymers. A plurality of digitally encoded images can be stored together or separately to form a database of digitally encoded images that are accessible individually or in combination. Such digitally encoded images can be altered using established methods, such as artistic renditions or image modulating software. A plurality of images can also be merged to form a new digitally encoded image.

"Solvent" refers to an aqueous, organic or inorganic solvent, such as water, isopropanol, tetrahydrofuran or acetone.

"Surfactant" refers to a surfactant as that term is known in the art, such as, for example, acetylene glycol or polyoxyethylene alkyl.

"Dispersant" refers to dispersants as they are known in the art, such as, for example, the Tergitol series from Union Carbide, polyoxylated alkyl ethers, alkyl diamino quaternary salts or "Pecegal "O"" from GAF (U.S. Pat. No. 5,560,766). Dispersants are preferably used at between about 0.1% and about 10%, more preferably between about 0.5% and about 5%.

"Lens" as used herein refers to a composition of matter that can transmit light. A lens preferably can act as an optical lens, such as a contact lens. In certain aspects of the present invention, a lens need not act as an optical lens, such as a contact lens that is used for therapeutic purposes as opposed to purposes relating to the correction, improvement or alteration of a user's eyesight.

"Contact Lens" refers to a structure that can be placed on or within a wearer's eye. A contact lens can correct, improve, or alter a user's eyesight, but that need not be the case. A contact lens can be of any appropriate material known in the art or later developed, and can be a soft lens, a hard lens or a hybrid lens. A contact lens can be in a dry state or a wet state.

"Soft Lens" refers to a variety of soft lenses as they are known in the art that are characterized as having, for example, at least one of the following characteristics: oxygen permeable, hydrophilic or pliable.

"Hard Lens" refers to a variety of hard lenses as they are known in the art that are characterized as having, for example, at least one of the following characteristics: hydrophobic, gas permeable or rigid.

"Hybrid Lens" refers to a variety of hybrid lenses as they are known in the art, such as, for example, a lens having a soft skirt and a hard center.

"Dry State" refers to an article of manufacture or a portion thereof in a state prior to hydration or the state of an article of manufacture or a portion thereof under storage or use conditions.

"Wet State" refers to an article of manufacture or a portion thereof in a hydrated state.

"Transparent" refers to a substantial portion of visible light transmitted through a structure, such as greater than or equal to 90% of incident light.

"Opaque" refers to a substantial portion of visible light reflected or absorbed by a structure, such as greater than or equal to 90% of incident light.

"Partially opaque" refers to a combination of transparent and opaque.

"Hydrogel" refers to a polymer that swells in an aqueous solution due to the absorbance of water. A hydrogel includes water or an aqueous solution as part of its structure.

"Polymer" refers to a linkage of monomers. Preferably, a polymer is a polymer appropriate for use in lenses, such as contact lenses. A polymer can be, for example, a homopolymer, a heteropolymer, a copolymer, a hydrophobic polymer, a hydrophilic polymer or any combination thereof.

"Hydrophobic Polymer" refers to a polymer that does not absorb an appreciable amount of water or an aqueous solution (see, U.S. Pat. No. 5,034,166).

"Hydrophilic Polymer" refers to a polymer that absorbs an appreciable amount of water or an aqueous solution (see, U.S. Pat. No. 5,034,166). Lens forming materials that are suitable in the fabrication of contact lenses are illustrated by one or more of the following U.S. Pat. Nos. 2,976,576; 3,220,960; 3,937,680; 3,948,871; 3,949,021; 3,983,083; 3,988,274; 4,018,853; 3,875,211; 3,503,942; 3,532,679; 3,621,079; 3,639,524; 3,700,761; 3,721,657; 3,758,448; 3,772,235; 3,786,034; 3,803,093; 3,816,571; 3,940,207; 3,431,046; 3,542,461; 4,055,378; 4,064,086; 4,062,624; and 5,034,166.

"Hydrophilic Monomer" refers to monomers used to make soft lenses, such as hydroxyethylmethacrylate, methacrylic acid, or N-vinylpyrrolidone (U.S. Pat. Nos. 5,271, 874; 5,272,010).

"Hydrophilic Monomer" refers to monomers used to make hard lenses, such as methylmethacrylate, ethoxyethylmethacrylate, styrene, or silicone (U.S. Pat. Nos. 5,271, 874; 5,272,010).

"Homopolymer" refers to a polymer comprising a single type of monomer such as hydroxyethylmethacrylate.

"Heteropolymer" refers to a polymer comprising more than one type of monomer such as hydroxyethylmethacrylate and methacrylic acid.

"Copolymer" refers to the use of two different polymers to make a polymer chain.

"Acrylic Polymer" or "Acrylics" refers to a variety of polymer of that genus and species as they are known in the art, such as, for example, hydroxyethylmethacrylate.

"Silicone Polymer" or "Silicones" refers to a variety of polymers of that genus and species as they are known in the art, such as, for example Tris (such as Tris (pentamethyldisiloxyanyl)-3-methacrylate-propylsilane or 3-methacryloxypropy tris(trimethylsiloxy)silane).

"Polycarbonate Polymer" or "Polycarbonate" refers to a variety of polymers of that genus and species as they are known in the art, such as, for example Lexan.

"Initiator" in the context of polymerization refers to an initiator as that term is known in the art, such as, for example, a chemical that starts a polymerization reaction.

"UV Initiator" in the context of polymerization refers to a UV initiator as that term is known in the art, such as, for example, a chemical that becomes reactive or active with the adsorption of energy, such as UV energy, such as, for example benzoin methyl ether.

"Binder" or "bonding agent" refers to compounds used perform the function of increasing the interaction between moieties, such as between monomers and polymers such as those terms are known in the art. Examples of binders or binding agents are hexamethylene diisocyanate or other isocyanate compounds.

"Thickener" refers to a compound that is used to increase the viscosity of a liquid or partially liquid mixture or solution such as that term is known in the art. An example of a thickener is polyvinyl alcohols.

"Anti-kogating agent" or "non-kogating agent" refers to compounds that facilitate printing processes that utilize nozzles, such as such terms are known in the art.

"Dispersant" refers to a surface-active agent added to a suspending medium to promote the distribution and separation of fine or extremely fine solid particles.

"Thermal Initiator" in the context of polymerization refers to a thermal initiator as that term is known in the art, such as, for example, a chemical that becomes active or reactive with the absorption of heat energy, such as, for example, Vazo-64 or azobisisobutyronitrile.

"Anti-Bacterial Agent" refers to a compound or composition that can act as a bactericidal or bacteriostatic or can reduce the growth rate of a bacteria such as tetrabutylammonium chloride.

"Anti-Fungal Agent" refers to a compound or composition that can act as a fungicidal or fungistatic or can reduce the growth rate of a fungi such as benzalkonium chloride salicylic acid.

"Disinfectant" refers to a compound or composition that can reduce the type, number or diversity of microorganisms.

"Humectant" refers to compounds that reduce evaporation, such as ethylene glycol.

"Printing" refers to the application of at least one printing formulation to a surface or structure. Printing can use any appropriate device or method known in the art of later developed for a particular purpose.

"Printing Device" refers to any appropriate device for printing on a surface or structure known in the art or later developed for a particular purpose. Preferably, a printing device includes the dispensation of microdroplets of liquid. The size or volume of the microdroplets can vary, but generally the smaller the microdroplet, the higher the quality of the printing produced. Preferred microdroplets are between about 1 picoliter and about 1,000 microliters, preferably between about 10 picoliters and about 10 microliters or between about 100 picoliters and about 1 microliter. Preferred microdroplets can also be in the microlieter range.

"Ink Jet Printing" refers to printing using a printing device that comprises at least one ink jet. Such printing devices are commercially available such as through, for example, Hewlett Packard Corporation (such as DeskJet 560C printer cartridges) and Encad Corporation.

"Piezo Printing" refers to printing using a printing device that comprises at least one piezo printing structure. Such piezo printing structures are known in the art, such as, for example, those available through Packard Instruments and Hewlett Packard Corporation or Canon Inc.

"Thermal Printing" refers to printing using a printing device that comprises at least one thermal printing structure. Such thermal printing structures are known in the art, such as, for example, those available through Hewlett Packard Corporation.

"Laser Printing" refers to printing using a printing device that uses at least one laser printing structure. Such printing structures are known in the art, such as, for example, those available through Cannon or Hewlett Packard Corporation.

"Pad Transfer Printing" refers to printing using a pad transfer printing device. Such pad transfer printing devices are known in the art, particularly for printing in the field of contact lenses. Briefly, a layer is placed or printed on a pad transfer device and the layer on the pad transfer device is transferred to another surface, such as a polymer or lens or other surface (U.S. Pat. No. 3,536,386 to Spivack, issued Oct. 27, 1970; U.S. Pat. No. 4,582,402 to Knapp, issued Apr. 15, 1986; U.S. Pat. No. 4,704,017 to Knapp, issued Nov. 3, 1987; U.S. Pat. No. 5,034,166 to Rawlings et al., Jul. 23, 1991; U.S. Pat. No. 5,106,182 to Briggs et al., issued Apr. 21, 1992; U.S. Pat. No. 5,352,245 to Su et al., issued Oct. 4, 1994; U.S. Pat. No. 5,452,658 to Shell, issued Sep. 26, 1995 and U.S. Pat. No. 5,637,265 to Misciagno et al., issued Jun. 10, 1997).

"Impregnation" refers to a drug being contacted with a surface, such as a polymer, and the drug diffuses into the polymer (EP 0357062 to Pfortner, published Mar. 7, 1990).

"Chemical Bond" refers to a covalent bond or non-covalent bond.

"Polymer-Polymer Bond" refers to two polymers forming covalent or non-covalent bonds, such as by cross linking polymers formed between two polymers, such as hydroxyethyl methylacrylate and ehtyleneglycoldimethacrylate.

"Dry State" refers to a polymer that is not fully hydrated.

"Wet State" refers to a polymer that is fully hydrated.

"Forming a Lens" or "Fabricating a Lens" refers to any method or structure known in the art or later developed used to form a lens. Such forming can take place, for example, using cast-molding, spin-casting, cutting, grinding, laser cutting, stamping, trimming, engraving, etching or the like (U.S. Pat. No. 4,558,931 to Fuhrman, issued Dec. 17, 1985).

"Cast-Molding" in the context of forming a lens refers to the formation of at least a portion lens using a mold (U.S. Pat. No. 3,536,386 to Spivak, issued Oct. 27, 1970; U.S. Pat. No. 3,712,718 to LeGrand et al., issued Jan. 23, 1973; U.S. Pat. No. 4,582,402 to Knapp, issued Apr. 15, 1986; U.S. Pat. No. 4,704,017 to Knapp, issued Nov. 3, 1987; U.S. Pat. No. 5,106,182 to Briggs et al., issued Apr. 21, 1992; U.S. Pat. No. 5,160,463 to Evans et al., issued Nov. 3, 1992; U.S. Pat. No. 5,271,874 to Osipo et al., issued Dec. 21, 1993 and EP 0357062 to Pfortner, published Mar. 7, 1990)

"Spin-Casting" in the context of forming a lens refers to the formation of a lens using centrifugal force (U.S. Pat. No. 3,557,261 to Wichterle, issued Jan. 19, 1971 and U.S. Pat. No. 5,034,166 to Rawlings et al., issued Jul. 23, 1991).

"Information Storage Medium" refers to any medium of expression that can store information in any appropriate format either permanently or transiently. Preferred information storage medium includes paper, electronic medium, magnetic medium or polymers, such as cyclo-olefin copolymers.

"Electronic Medium" refers to information storage medium that can store information in electronic form. For example, electronic medium includes magnetic storage medium, such as diskettes.

"Machine Readable Format" refers to information stored on or within an information storage medium in a form, language or arrangement such that a machine, such as a central processing unit (CPU) can access and use the information.

"Database" refers to a collection of information, such as digital images. The information is preferably provided on or within an information storage medium and can be separate from or integral with a central processing unit.

"Printable formulation" refers to a printable formulation that can be used in conjunction with a printing technology or printing device to provide at least one structure, at least one layer, or a combination thereof, of the present invention.

"Subject" refers to, but is not limited to, a human or non-human primate; a companion animal such as but not limited to a dog, a cat, a bird, a fish, a reptile, an amphibian, a fox, a wolf, a pig, a horse or other companion as is known in the art; laboratory animal, such as, but not limited to a mouse, a rat, a guinea pig, a rabbit, a dog, a cat, a ferret, a pig, or other laboratory animals as is known in the art; working animals such as but not limited to a dog, a horse or other working animals as are known in the art; or any other animal as in known in the art that may be in need of the technology of the present invention or for testing of the technology of the present invention.

"Digital printing" refers to the printing of at least a portion of a layer of the present invention using at least one digital image printing technology.

"3D printing" or "three dimensional printing" refers to the printing of three-dimensional structures using appropriate printing technologies and printers as are known in the art or later developed. 3D printing is useful in the making of parts, products or layers using a computer-driven, additive process, one or more layers at a time. 3D printing can build parts or other structures such as layers, using any appropriate material, such as, but not limited to plastic or metal, directly from CAD drawings or other digital images that have been preferably cross sectioned into may, if not hundreds or thousands of layers. 3D printing provides a faster and less costly alternative to machining, such as but not limited to machining, including but not limited to cutting, turning, grinding and drilling of materials, such as solid materials. Although various techniques are used in 3D printing in the relevant art, 3D printers use method of additive fabrication, that is the building a part or structure one layer at a time, with layers ranging in thickness from about a millimeter to less than $1/1,000$ of an inch. The building material can be in any appropriate form, such as, but not limited to a liquid, a power or a sheet of material that is cured by heat, UV light, a chemical reaction or other appropriate method.

Other technical terms used herein have their ordinary meaning in the art that they are used, as exemplified by a variety of technical dictionaries.

Introduction

The present invention recognizes that medical devices, such as but not limited to contact lenses, can be made having at least one coating made at least in part using printing technologies to provide drug storage and drug release structures, notably for hydrophobic drugs and that such hydrophobic drugs can be stabilized as to hydrolysis, heat, and a combination thereof.

As a non-limiting introduction to the breath of the present invention, the present invention includes several general and useful aspects, including:

1) A medical device including a medicament, in general.
2) A method of making a medical device including a medicament, in general.
3) A method of using a medical device of the present invention to treat or prevent a disease, disorder or condition, in general.
4) A packaged medical device that includes at least one drug delivery contact lens. 5) A drug delivery contact lens.
6) A method of making a drug delivery contact lens.
7) An ink.
8) A method of using a drug delivery contact lens to treat or prevent a disease, disorder, or condition of the eye.

These aspects of the invention, as well as others described herein, can be achieved by using the methods, articles of manufacture and compositions of matter described herein. To gain a full appreciation of the scope of the present invention, it will be further recognized that various aspects of the present invention can be combined to make desirable embodiments of the invention.

I. Medical Devices Including a Medicament—in General

The present invention includes an article of manufacture that includes: a) a medical device including at least one surface; and b) one or more coatings provided on at least a portion of the at least one surface. The one or more coatings can include at least one drug.

Furthermore, U.S. Pat. Nos. 9,931,296 and 10,413,506, all to Doshi generally relate to medical devices including a medicament, notably drug delivery contact lenses, and are incorporated by reference herein, notably for the purpose of medical devices including a medicament, notably drug delivery contact lenses.

A. Medical Device

The medical device of the present invention can be any known in the art or later developed. The medical device can be implanted within a subject as is the case with many medical devices as they are known in the art such as, for example, cardiac stents, joint replacements such a hip and knee among others, birth control sticks, pacemakers, breast implants, facial implants for reconstructive or cosmetic purposes such as for the cheeks and chin, intrauterine devices (IUD's), pins and mesh and resorbable materials such as known in the art (such as, but not limited to, polylactic acid (PLA)) for bone reconstruction or immobilization, dental implants, filters to entrap blood clots in blood vessels, optical lens replacements for cataract treatment, voice boxes for throat cancer patients and the like.

The medical device of the present invention can also be non-implantable as they are know in the art, such as, for example, contact lenses, dental apparatus, drug patches, transdermal drug patches including but not limited to birth control, Alzheimer's patches, smoking cessation patches, hearing aids, earplugs or other devices inserted into the ear to treat swimmer's ear and ear infections and the like.

The medical device of the present invention can be made of any appropriate material or combination of materials as appropriate for the purpose and location where the medical device will ultimately reside within or on a subject. The choice of materials for the medical device is determinable by one skilled in the art, and there are numerous examples in the prior art for the skilled artisan to follow. For the present invention, it is generally the surface of the medical device on which a coating is provided, but this need not be an exclusive requirement.

B. Surface

The surface of a medical device that is to be coated in the manner of the present invention can be of any appropriate material and is usually determined or influenced by the nature of the medical device and where, and how long, it is to be implanted, or not implanted, within or on a subject.

Many medical devices present metal on their surface. Examples include, but are not limited to, bone pins and mesh for bone repair and stabilization. Metals that can be used as a surface include, for example, steal, stainless steel, gold, silver and the like.

Some medical devices present a plastic or polymer on their surface. Examples include but are not limited to contact lenses, IUD's an implantable birth control sticks. There are a wide variety of polymers and plastics available for use in medical devices, which are too numerous to enumerate here. Individual polymers and plastics are discussed further herein, and are intended as a limiting list of such materials.

Other medical devices present partially polymerized polymers during their manufacture, but not necessarily in the final product. The partially polymerized polymers can be used as an intermediate product to facilitate bonding with other components of the device. Examples include, but are not limited to, contact lenses and the like.

Still other medical devices present on their surface polymer matrices. Examples include, but are not limited to, limited to materials that allow for skin or other tissue regenerations, such as for trauma, disease, disorder, condition such as, for example, burn treatment, such as those that contain fibronectin or other structural proteins. The polymer matrix or protein matrix can be any appropriate, such as but not limited to proteins, nucleic acids, and carbohydrates.

In addition, still other medical devices present on their surface silicone, ceramic, glass, carbon (inclusive of nanotubles and graphite) and fabric. Examples include, but are not limited to, breast implants, penal implants, hip replacement parts, knee replacement parts, bandages for burn and trauma wounds, and the like. The silicone, ceramic, glass, carbon (including but not limited to graphite including sheets, carbon nano-structures such as tubes, balls, sheets and other structures) and fabric can be any appropriate and as are realized in the art.

The surface of a medical device can also be pretreated or modified by various processes to, in some instances, clean or otherwise prepare the surface for receiving the coating of the present invention. Some pretreatments may be physical in nature, such as polishing, scarring or scoring, whereas others may be chemical in nature. Preferred chemical process include, but are not limited to, chemical coating, chemical cleaning, chemical texture modification, chemical or electrochemical activation or creation of reactive groups on or within said at least one surface, application of one or more chemicals to said at least one surface, and combinations thereof.

C. Drug Reservoir Layer

The drug reservoir layer serves to store a drug for later release from the coating. The drug reservoir layer is preferably porous or otherwise is able to contain a drug for this purpose. In one aspect of the present invention, the drug reservoir layer is solid or semi-solid, such as a gel or sol, which can reversibly entrap a drug for later release. The drug reservoir layer can be provided first without a drug and the drug added at a later step. In the alternative the drug reservoir layer can be provided with a drug in one step. The drug reservoir layer is preferably made using printing technology. The choice of polymer depends on several factors, including, for example, the printing technology to be used to print the drug reservoir layer.

The drug reservoir layer can include a polymer with the characteristics stated above. Preferable polymers include, but are not limited to, polyHEMA, polyGMA, polyvinylalcohol, polyDMA, PMMA (polymethylacrylicacid), polycarbonate, PVP (polyvinylpyrolidone), siloxane, and the like. Depending on the polymer and the printing technology chosen, the polymer can be provided in a monomer state and later polymerized, or in the alternative, provided in a partially polymerized state.

The drug reservoir layer can also include a partially polymerized polymer with the characteristics stated above and can be any as appropriate. Preferable polymers include, but are not limited to polyHEMA, polyGMA, polyvinylalcohol, polyDMA, PMMA (polymethylacrylicacid), polycarbonate, PVP (polyvinylpyrolidone), siloxane, and the like. Depending on the partially polymerized polymer and the printing technology chosen, the partially polymerized polymer can be provided in a monomer state and later partially polymerized, or in the alternative, provided in a partially polymerized state.

The drug reservoir layer can include a polymer matrix with the characteristics stated above and can be any as appropriate. Preferable polymer matrix include, but are not limited to, proteins, nucleic acids, and carbohydrates. Depending on the polymer and the printing technology chosen, the polymer matrix can be provided in a monomer state and later polymerized, or in the alternative, provided in a polymerized state.

In addition, still other materials can be used for the drug reservoir layer, such as, but not limited to silicone, ceramic, glass, carbon (inclusive of nanotubles and graphite) and fabric. The silicone, ceramic, glass, carbon and fabric can be any appropriate and as are realized in the art and the choice generally relates, as with other materials used in the drug reservoir layer, to they physical characteristics such as the ability to accept and retain a drug for later release and the printing technology chosen to print the drug reservoir layer.

Preferable materials for the drug reservoir layer include derivatized oligomers. Preferable derivatized oligomers include, but are not limited to HEMA (mydroxyethylmethylacrylates), DMA (dimethylacrylamides), GMA (glycidolmethylacrylates), PVA (polyvinlyalcohols), silicone or siloxane. As with other materials used, the choice of derivatized oligomers depends on the physical characteristics of the material and the printing technology used to make the drug reservoir layer.

If the material used for the drug reservoir layer need to be polymerized and cured, then a polymerization initiator or curing initiator needs to be used. The requirement for a polymerization initiator or curing initiator depends on the particular type of polymer/monomer being utilized and the choice is established in the technology. Preferable polymerization initiator or curing initiators include, but are not limited to at least one of UV cure, thermal cure, room temperature cure, simultaneous printing and UV curing or e-beam.

As set forth in the figures, the drug reservoir layer can release a drug in one or more directions. For example, turning to a contact lens, the drug receiving layer can release drug towards the cornea or towards the eyelid when the contact lens is engaged with the eye. The use of layers, or lack thereof, allows for the design of structures that allow drug to be released in one or both directions.

The material used for the drug receiving layer can be bonded to, permanently bonded to, or not bonded to the surface. Certain materials that can be used for the drug reservoir layer inherently bond or do not bond to a surface, depending on the nature of the surface. As discussed previously, the surface can be modified, such as through chemical medication or other methods or techniques, to allow the drug reservoir layer to chemically bond or react with the drug receiving layer components.

D. Drug Receiving Layer

The manufacture of the drug reservoir layer can include the use of a drug receiving layer. In this instance, a drug receiving layer is applied to the surface by an appropriate means or method, such as printing. The drug receiving layer could include or not include a drug at this juncture in time. The drug receiving layer has physical and chemical characteristics to allow the efficient and localized acceptance of a drug applied thereto using appropriate methods, preferably printing. Once the drug receiving layer is applied to the surface, then a drug, or an additional drug, is applied thereto to entrap the drug or additional drug therein for later release.

The drug receiving layer can be of any appropriate material with the appropriate physical and chemical characteristics to obtain a structure with the desired characteristics discussed herein. The drug receiving layer can be a chemical. Preferred materials for the drug receiving layer include, but are not limited to, a highly absorbent polymer such as, but not limited to, a polyvinlylpyrrolidone homopolymer, a polyvinylpyrrolidone copolymer, a polyacrylamide homopolymer, a polyacrylamide copolymer, a polyacrylate homopolymer, a polyacrylate copolymer, a proteinaceous material, a carbohydrate, or a combination thereof.

As there may be other layers applied to the surface prior to the drug receiving layer, the drug receiving layer can be applied to such prior layers using appropriate methods. As with other layers of the coating of the present invention, the drug receiving layer can be provided by any appropriate method, preferably by printing technology.

Where the drug receiving layer includes a polymer, then the drug receiving layer can include a bonding agent or crosslinking agent in order to aid in entrapping or otherwise immobilizing a drug for later release from the drug reservoir layer. Preferable bonding agents include, but are not limited to methylacrylic acid, titanates, and silanes. Preferable crosslinking agents include, but are not limited to HDI, and devivitized oligomers of HEMA, GMA, DMA and PVA, Polyfunctional Aziridine, and multifunctional carbodimide.

In one preferred aspect of the present invention, the drug receiving layer includes a highly absorbent polymer. Preferred highly absorbent polymers include, but are not limited to a polyvinylpyrrolidine homopolymer, a polyvinylpyrrolidone copolymer, a polyacrylamide homopolymer, a polyacrylamide copolymer, a polyacrylate homopolymer, a polyacrylate copolymer, a proteinaceous material, a carbohydrate, or a combination thereof.

The preferred method of application of a drug receiving layer of the present invention is printing technologies and coating technologies. Preferable methods of printing include, but are not limited to direct coating, application of droplets or microdroplets, ink jet printing, soaking, impregnation, spin coating, drip coating, screen coating, silk screen coating, or pad printing such as those methods are known in the art.

E. Drug

The drug provided in the drug reservoir agent is a matter of choice to one skilled in the appropriate arts depending on the disease, disorder or condition to be treated or prevented, along with the location of the article of manufacture on or with the subject and the nature of the medical device used. For example, drug for the treatment or prevention of glaucoma would be provided with a contact lens, whereas a drug for the treatment or prevention of restinosis would be provided with a stent.

The drug released from the article of manufacture should be of the appropriate amount, duration and dosing in order to be an effective amount to prevent or treat at least one disease, disorder or condition. The amount, duration and dosing of a drug to a particular location for such treatment or prevention is available to one skilled in the art. The present invention allows localized and controlled dosing in terms of the amount and duration of the dose and can allow for the continuous or intermittent release of drug for a regime of drug delivery.

One preferable aspect of the present invention is the delivery of a drug to the eye to treat or prevent or treat diseases, conditions or disorders of the eye. There are drugs known to treat or prevent a variety of diseases and conditions with appropriate regimes of dose, time course of administration, and route of administration. The present invention allows for varying the regime of dose and time course and provides a highly localized route of administration as well. Preferred drugs that are antibiotics useful for treatment of eye infections include, but are not limited to, gentamicin, tobramycin, erythromycin, polytrim, cirproflizacin, viamox, and xymar. Preferred drugs that are used to treat glaucoma include, but are not limited to, timolol, alphagan, axopt, cosopt, lumigan, travatan, xalatan, and combigan. Preferred drugs that are ani-inflammatory that are used to treat diseases, disorders and conditions of the eye include, but are not limited to, perdforte, lotemax, fluromethlone, nevanac, acular and xibrom. Other drugs known in the art to treat or prevent diseases, conditions or disorders of the eye include, but are not limited to pilocarpine, dexamethasone, pilocarpine nitrate, tropicamide, timolol, timolol nitrate, timolol maleate, methyl prednisolone, flurbiprofen, penillin G, gentamicin, ciprofloxacin, tobramycin, sulphacetaminde sodium, indomethacin, hydrocortisone, indomethacin, pilocarpine hydrochloride, ciprofloxacin hydrochloride, insulin, indomethacin, and ketorolac tromethamine, either alone or in combination. (See, for example, Yasmin Sultana, Rahul Jain, Rahul Rathod, Asgar Ali, M. Aqil, Department of Pharmaceutics, Faculty of Pharmacy, Hamdard University, New Delhi 110062, INDIA. "Advances in Ophthalmic Drug Delivery Systems: Part I" By—Apr. 12, 2005, in Latest Reviews Vol. 3 Issue 2, 2005, www.pharmmainfo.net/reviews/advances-ophthalmic-drug-delivery-systems-part-i, and Yasmin Sultana, Rahul Jain, Rahul Rathod, Asgar Ali, M. Aqil, Department of Pharmaceutics, Faculty of Pharmacy, Hamdard University, New Delhi 110062, INDIA, "Advances in Ophthalmic Drug Delivery Systems: Part II" By—Apr. 12, 2005, in Latest Reviews Vol. 3 Issue 2, 2005, www.pharmmainfo.net/reviews/advances-ophthalmic-drug-delivery-systems-part-ii (Apr. 1, 2011) ("Sultana et al. Part II). Sultana et al. Part I and Sultana et al. Part II provide reviews and listings of drugs and combinations thereof to treat or prevent various diseases, conditions and disorders of the eye. The patent literature also provides for ocular drug delivery devices and strategies as provided by Sultana et al. Part I and Sultana et al. Part II. See, for example US patent and US published patent application numbers: U.S. Pat. Nos. 4,925,581; 5,227,372; 5,296,228; 5,480,914; 5,578,638; 5,705,194; 5,888,493; 6,242,442; 6,297,240; 6,316,441; 6,410,045; 6,416,740; 20020071874; 20020197300; 20030017199; 5,837,226; 6,017,875; 6,154,671; 6,217,896; 6,319,240; 6,335,335; 6,410,045; 6,539,251; 6,579,519; 20020026176; 20030147849; 20020064513; 20020114778; 20020119941; 20020197300; 20030175324; 20030185892; 20030191426; and 20040037889.

In one aspect the present invention, the drug is provided in the drug reservoir layer and released from the drug receiving either alone or in combination with other ingredients. Alternatively, the drug can be provided in the drug reservoir layer with such other ingredients and then released from the drug reservoir layer without such other ingredients. In a preferred aspect of the present invention the drug is provided at least in part as a sole active ingredient without any other ingredient association that can alter the activity or deliverability of the at least one drug. That is to say that the drug is provided or released alone and free of other ingredients, such as but not limited to those used for encapsulation, micro-encapsulation or emulsification of a drug.

The drug can be provided or released from the drug receiving layer and coating of the present invention in an encapsulated form. Encapsulation of drugs is known in the art, such as and is within the skill of the ordinary artisan. Preferred encapsulation materials include, but are not limited to: biodegradable polycyanoacrylate, biodegradable poly(alkylcyanoacrylates), biodegradable calcium phosphate, legumin, polysaccharides drafted with polyesters (amphyphilic copolymers), poly(methylidene malonate), gelatin, poly(E-caprolactone), sodium alginate, agarose hydrogel, PMMA, biotinylated poly(ethylene glycol) conjugated with lactobionic acid, poly(vinyl alcohol) hydrogel, biotinylated pullulan acetate, dib loc copolymers and mixtures thereof. Wherein the polycyanoacrylates are preferably, but not limited to: polybutylcyanoacrylate, polyhexylcyanoacrylate, polyethyl-cyano-acrylate, polyisobutylcyanoacrylate and mixtures thereof.

The drug can be provided or released from the drug receiving layer and coating of the present invention in a micro-encapsulated form. Micro-encapsulation of drugs is known in the art, such as "Microencapsulation Techniques, Factors Influencing Encapsulation Efficiency: A Review" Jyothi et.al Journal of Microencapsulation, Informa Health Care, Volume 27, Issue 3, P. 187-197, and is within the skill of the ordinary artisan.

The drug can be provided or released from the drug receiving layer and coating of the present invention in a nanoencapsulated with an encapsulation material in nanoparticles. Nanoencapsulation of drugs is known in the art and is within the skill of the ordinary artisan. Non-limiting examples of nanoencapsulation materials include: chitosan nanparticles, human serum albumin nanoparticles; silica nanospheres, PEG'ylated core-shell nanoparticles, biodegradable PGGA (poly(D,L-lactide-co-glycolide) particles, PLA (poly lactic acid), PGA, PLG (poly-(D,L-glycolide) polymeric nanoparticles, biocompatible gliadin nanoparticles, low pH sensitive PEG stabilized plasmid-lipid nanoparticles, tocopherol derivatives stabilized nano-sized emulsion particles, PLA-PEG nanoparticles, nanoparticles composed of hydrophilic proteins coupled with apolipoprotein E, biodegradable poly(vesiln-caprolactone) nanoparticles, biotinylated poly(ethylene glycol) conjugated with lactobionic acid, carboxylmethyl dextran magnetic nanoparticles and mixtures thereof.

The drug can be provided or released from the drug receiving layer and coating of the present invention in an emulsion, water-in-oil emulsion, an oil-in-water emulsion, or a liposome. Emulsions, water-in-oil emulsions, oil-in-water emulsions and liposomes including drugs is known in the art, such as U.S. Pat. No. 7,638,137 B2, and is within the skill of the ordinary artisan.

The drug of the present invention can take any appropriate form, such as a small molecule or a biologic or biologic mimic as those terms are known in the art. As stated previously, a wide variety of drugs in many forms are known for the treatment or prevention of a disease, disorder or condition. The present invention is not limited to any particular type or classification of drug. The structures of the coating of the present invention can be tailored for the storage and release of any appropriate drug. For example, the porosity of a drug reservoir layer would tend to be greater for a larger molecule, and likewise less so for a small molecule. By way of example, a small molecule would include hormones for hormone replacement therapy or nucleoside analogues as anti-viral agents. Biological drugs and related biological mimics, by way of example, would include the general classifications of enzymes, transport proteins, structural proteins, storage proteins, hormone proteins, receptor proteins, contractile proteins, defensive proteins, cytokines, clotting factors and vaccines. An example of a preferred proteins include, but are not limited to, insulin for the treatment of diabetes and antibodies and monoclonal antibodies for the treatment of infection or for targeted delivery of associated drugs.

In essence, virtually any drug can be useful in the present invention and an enumerated listing is beyond the scope of this document. As way of example, the following is a non-limited and non-exhaustive list of general classifications of drugs useful in the present invention: an anti-inflammatory, an anti-allergy, and antibiotic, a drug for the treatment of glaucoma, a drug for the treatment of macular degeneration, an ophthalmic drug, a hydrophilic drug, a hydrophobic drug, an anti-parasitic drug, a steroid, an antibiotic and a medicament for the treatment of dry eye and a medicament for treatment of eye discomfort.

F. Printing

A wide variety of printing technologies are applicable to providing the various layers of the coating of the present invention. The choice of which printing technology to use is a matter of choice for the skilled artisan based on the particular size, shape, thickness and other characteristics of the layer being provided. In addition, as some of the layers are printed in liquid or semi-solid form and then transformed into a solid or semi-solid form by, for example but not limited to polymerization or partial polymerization, the characteristics of the printing liquid or semi-solid is to be taken into account. As a preferred aspect of the present invention, the compositions of Doshi et al., published U.S. application No. 2008/0062381A1, published Mar. 13, 2008, are applicable, particularly when the pigment is optionally present in such formulations, and at least one drug is optionally provided in such formulations.

Preferred printing methods are digital in nature, such as those described by Doshi et al. (U.S. 2008/0062381A1) which is incorporated by reference herein in its entirety, such that they allow for a relatively precise method and means to provide a high quality and well defined print product. As the method and associated device are digital in nature, the printing process is adaptable for computer control and product design. Preferred digital printing methods and structures are discussed herein. As a non-limiting introduction to digital printing methods and devices, the following digital printing methods are preferred: ink jet printing, three dimensional printing (3D printing), piezo printing, thermal printing, laser printing MEMS printing (Micromached Electro-Mechanical System) wherein the printing head or related or associated structures are rotatable or non-rotatable. Generally, but not exclusively, a printing solution of the present invention replaces the ink solution of existing and commercially available printing devices, in particular within the printing cartridge.

Likewise, preferred printing methods include pad printing as those methods are known in the art, including but not limited to pad transfer printing. Pad printing is not as exact as digital printing, but is a preferred method of printing for the present invention. Pad printing is known in the art for printing of images of the iris of the eye on contact lenses (see, for example, U.S. Pat. Nos. 5,302,978, 5,414,477, and 4,668,240).

Ink jet printing is known in the art and can take various forms and associated structures as are discussed herein. Generally, ink jet printing refers to printing devices and methods that utilize highly precise printing methods and structures that allow for the production of high quality and precise structures. Generally, available ink jet printing devices and structures can be utilized with minimal modification, with the ink solutions normally present in the ink jet cartridge or reservoir is replaced with a solution that includes a polymerizable monomer and associated polymerization initiators as needed. The polymerizable monomer can be polymerized at will and at a rapid rate after being dispensed from the ink jet printing structure.

Three dimensional printing is based primarily, but not exclusively, on ink jet printing technologies. These methods and devices allow for the generation of one-off or multiple copies of structures. Generally, a polymerizable solutions is placed within the printing device and is dispensed under computer control and polymerized in repeated printing cycles or steps to generate a three dimensional structure. Examples of available and preferred 3D printing devices and related structures and cartridges include, but are not limited to, those disclosed herein and otherwise known in the art or later developed.

Piezo printing is a subtype of ink jet printing that is a preferable printing method of the present invention. Examples of available and preferred piezo printing devices and related structures and cartridges include, but are not limited to, those disclosed herein and otherwise known in the art or later developed.

Thermal printing is a subtype of ink jet printing that is a preferable printing method of the present invention. Examples of thermal printing devices and related structures and cartridges include, but are not limited to, those disclosed herein and otherwise known in the art or later developed.

Laser printing is a subtype of ink jet printing that is a preferable printing method of the present invention. Examples of laser printing devices and related structures and cartridges include, but are not limited to those disclosed herein and otherwise known in the art or later developed.

Optionally, an ink jet printing device can include a rotating printer head that can allow for enhanced printing on curved surfaces.

Another preferred printing method is MEMS printing, wherein MEMS stands for Micromached electromechanical system and is based on technologies that allow for the printing of integrated circuit boards, but are applicable to the production of very small structures that have functionality. Examples of structures having functionality made by MEMS printing include mechanical gears and other mechanical devices, lab on a chip structures for the performance of laboratory procedures including chemical reactions and diagnostic procedures G. Modulation of Release of Drug The combination of the components of the coating of the present invention, in particular the at least one drug reservoir layer that includes at least one drug allows for the controlled release of the at least one drug from the coating. The coating structure allows for the production of a coating layer that can particularly tailor the release of the at least from drug from the coating layer for desirable characteristics, such as, but not limited to, dose, regime, time course of delivery and route of administration. As the article of manufacture can be localized to a particular locus on a subject, the drug can be delivered with particular focus with a particular regime, which can allow for less drug being administered to a subject if it were otherwise administered in a more systematic route of administration. The particular physical chemistry phenomenon associated with the release of the drug from the coating layer are discussed herein, but the listing is not to be considered limiting.

In one aspect of the invention, the release of the at least one drug from the coating layer can be modulated by diffusion out of the drug reservoir layer. Determination of the effect of diffusion on the migration of a chemical entity out of a substrate can be made using established methods, formulas and through routine experimentation.

In another aspect of the invention, the release of the at least one drug from the coating layer can be modulated by diffusion out of the drug reservoir layer. Determination of the effect of diffusion on the migration of a chemical entity out of a coating layer of the present invention can be made using established methods, formulas and through routine experimentation.

In another aspect of the invention, the release of the at least one drug from the coating layer can be modulated by mass action out of the drug reservoir layer. Determination of the effect of mass action on the migration of a chemical entity out of a coating layer of the present invention, can be made using established methods, formulas and through routine experimentation.

In yet another aspect of the invention, the release of the at least one drug from the coating layer can be modulated by a concentration gradient of the at least one drug out of the drug reservoir layer. Determination of the effect of a chemical gradient on the migration of a chemical entity out of a coating layer of the present invention, can be made using established methods, formulas and through routine experimentation.

In yet another aspect of the invention, the release of the at least one drug from the coating layer can be modulated by the solubility of the at least one drug in an environment out of the drug reservoir layer. Determination of the effect of a solubility on the migration of a chemical entity our of a coating layer of the present invention, can be made using established methods, formulas and through routine experimentation.

In yet another aspect of the invention, the release of the at least one drug from the coating layer can be modulated by the temperature at which the article of manufacture is held (either at storage temperature or during use) of the at least one drug out of the drug reservoir layer. Determination of the effect of temperature on the migration of a chemical entity out of a coating layer of the present invention, can be made using established methods, formulas and through routine experimentation.

In yet another aspect of the invention, the release of the at least one drug from the coating layer can be modulated by the molecular weight of the at least one drug out of the drug reservoir layer. Determination of the effect of molecular weight on the migration of a chemical entity out of a coating layer of the present invention, can be made using established methods, formulas and through routine experimentation.

In yet another aspect of the invention, the release of the at least one drug from the coating layer can be modulated by a concentration gradient of the at least one drug out of the drug reservoir layer. Determination of the effect of the migration of a chemical gradient on a chemical entity out of a coating layer of the present invention, can be made using established methods, formulas and through routine experimentation.

In further aspect of the invention, the release of the at least one drug from the coating layer can be modulated by the thickness of the coating layer, and the components thereof, namely the drug reservoir layer. Determination of the effect of the thickness of the coating and the components thereof on the migration of a chemical entity out of a coating layer of the present invention, can be made using established methods, formulas and through routine experimentation.

In a still further aspect of the invention, the release of the at least one drug from the coating layer can be modulated by the porosity of the coating layer, and the components thereof, namely the drug reservoir layer. Determination of the effect of the porosity of the coating and the components thereof on the migration of a chemical entity out of a coating layer of the present invention, can be made using established methods, formulas and through routine experimentation.

In a still further aspect of the invention, the release of the at least one drug from the coating layer can be modulated by the pore size of the coating layer. Determination of the effect of the pore size of the coating layer and the components thereof on the migration of a chemical entity out of a coating layer of the present invention, can be made using established methods, formulas and through routine experimentation.

In a still further aspect of the invention, the release of the at least one drug from the coating layer can be modulated by the molecular exclusion size of the coating layer, and the components thereof, namely the drug reservoir layer. Determination of the effect of the molecular exclusion size of the coating and the components thereof on the migration of a chemical entity out of a coating layer of the present invention, can be made using established methods, formulas and through routine experimentation.

In another aspect of the invention, the release of the at least one drug from the coating layer can be modulated by the water content of the coating layer, and the components thereof, namely the drug reservoir layer. Determination of the effect of the water content of the coating and the components thereof on the migration of a chemical entity out of a coating layer of the present invention, can be made using established methods, formulas and through routine experimentation.

In yet another aspect of the invention, the release of the at least one drug from the coating layer can be modulated by the concentration of the drug in the coating layer, and the components thereof, namely the drug reservoir layer. Determination of the effect of the concentration of the drug in the coating and the components thereof on the migration of a chemical entity out of a coating layer of the present invention, can be made using established methods, formulas and through routine experimentation.

In a further aspect of the invention, the release of the at least one drug from the coating layer can be modulated by the concentration of the drug in the coating layer, and the components thereof, namely the drug reservoir layer. Determination of the effect of the concentration of the drug in the coating and the components thereof on the migration of a chemical entity our of a coating layer of the present invention, can be made using established methods, formulas and through routine experimentation.

In a still further aspect of the invention, the release of the at least one drug from the coating layer can be modulated by the packaging environment of the coating layer (such as the concentration of drug in the packaging solution, if present), and the components thereof, namely the drug reservoir layer. Determination of the effect of the packaging environment of the coating and the components thereof on the migration of a chemical entity our of a coating layer of the present invention, can be made using established methods, formulas and through routine experimentation.

In one aspect of the invention, the drug can exhibit sustained release over time from the coating layer. This can be achieved by first establishing the relationship of release rate of a given drug for a given material of layer in terms of thickness variation, drug solubility, concentration. In another aspect of the invention, the drug can exhibit intermittent release over time from the coating layer.

In yet another aspect of the invention, more than one drug can be released from the coating layer of the present invention. In the alternative, more than one drug can be provided in a single drug reservoir layer.

H. Contact Lens

In one preferred aspect of the present invention, the medical device includes a contact lens. Contact lenses that include a drug, on the surface of the contact lens or within the contact lens are known in the art. However, these contact lenses do not provide the structures of the present invention, such as the at least one coating that includes at least one drug reservoir layer that can include at least one drug, and at least one layer that can include structures, wherein the release of the at least one drug from the at least one coating layer is modulated by A variety of materials are known in the art for making contact lenses and are useful in the present invention. Preferred materials include, but are not limited to, acrylics, silicones, polyvinylalcohols, and combinations thereof.

There are a variety of general types of contact lenses known in the art and are useful in the present invention. Preferred general types of contact lenses include, but are not limited to hybrid lenses, hydrophilic lenses and hydrophilic lenses.

In addition, there are other general types of contact lenses known in the art and are useful in the present invention. These lenses include, but are not limited to spherical lenses, toric lenses, multifocal lenses, tinted lenses, corrective optical power lenses and lenses without corrective optical power.

There are a variety of methods used to make lenses that are useful in the present invention. Preferred methods of making, at least in part or in combination, contact lenses include, but are not limited to, lathing, cast molding, spin casting and ink jet printing.

Once a contact lens is manufactures, a variety of secondary or finishing operations can be utilized and are useful in the present invention. Preferred secondary or finishing operations include, but are not limited to edging, polishing, tinting, hydration, extraction, and sterilization.

In one aspect of the present invention, the at least one drug in an at least one coating layer can be provided on the surface of a contact lens. In another aspect of the present invention, the at least one drug in at least one coating layer can be provided within a contact lens. In another aspect of the present invention, the at least one drug can be provided inside a contact lens without the structures in an at least one coating layer in combination with at least one drug in at least one coating layer on the surface of a lens. In yet another aspect of the present invention, the at least one coating layer with at least one drug can be provided both on the surface of the lens and inside the lens.

In some cases, drugs provided within the at least one coating can have optical properties that can interfere with the optical function of the contact lens, such as drugs having coloring or opaqueness. Preferred drugs for use in the present invention do not have such optical properties, but that need not be the case as drugs having such optical properties are useful in the present invention.

In another aspect of the present invention, the one or more coatings can optionally dispersed therein nanoparticles having a particles size less than about 50 nm, a nanoencapsulated ophthalmic drug from which the ophthalmic drug is able to diffuse into and migration through the contact lens and into the post-lens tear film or towards the eyelid when the contact lens is placed on the eye, the nanoparticles being disperse within the contact lens or on at least one surface of the contact lens in an amount such that the lens optionally remains substantially optically transparent (see, for example, U.S. Pat. No. 7,638,137B2 to Chauhan et al., issued Dec. 29, 2009).

In another aspect of the present invention, the one or more coatings can optionally dispersed therein nanoparticles having a particles size less than about 50 nm, a nanoencapsulated ophthalmic drug from which the ophthalmic drug is able to diffuse away from and migrate away from the contact lens and into the post-lens tear film or towards the eyelid when the contact lens is placed on the eye, the nanoparticles being disperse within the contact lens or on at least one surface of the contact lens in an amount such that the lens optionally remains substantially optically transparent (see, for example, U.S. Pat. No. 7,638,137B2 to Chauhan et al., issued Dec. 29, 2009).

In yet another aspect of the present invention, when the at least one drug is provided with or without a drug delivery compositions as described herein, the at least one drug as provided with or without a drug delivery compositions is substantially optically transparent. However, this need not be the case. In one aspect of the present invention, when the at least one drug as provided with or without a drug delivery composition is substantially optically transparent or is not substantially optically transparent, the optical characteristics of the at least one drug, or other structures of the at least one coating layer, can be masked with opaque material or tinting, such as color tinting as is known in the art.

I. Packaging

The article of manufacture of the present invention can be provided in a variety for forms and packaging formats and solutions as present. Many of these packaging form and formats are established packaging formats, whereas others are unique to the present invention.

The article of manufacture of the present invention can be provided in a packaging in a dry state, preferably in a dehydrated state or a lyophilized state using methods know in the art. The article of manufacture of the present invention can also be provided in a packaging in a wet state, that is to say provided in an appropriate solution and, as appropriate, in a hydrated state.

The format of the packaging can be any as is appropriate. For example, the article of manufacture can be provided in packaging that is appropriate and normal for the article of manufacture, such as vials, other containers such as boxes or plastic containers, or in vials. Vials and blister packaging are preferable, but not necessary, for example, for contact lenses.

The solution present, if any, in a packaging format, in particular for a wet state packaging format can include the at least one drug present in the at least one coating layer, a different drug that that provided in the coating layer, or a combination thereof.

In one instance, the concentration of the drug in a packaging solution is less than the concentration of the drug in the coating layer. In that case, it is likely that the drug in the coating layer may migrate from the coating layer into the packaging layer and eventually reach a steady state equilibrium state, but that not be the case.

In another instance, the concentration of the drug in a packaging solution is equal to the concentration of the drug in the coating layer. In that case, it is likely that the drug in the packaging solution will be in steady state with the drug in the coating layer, but that need not be the case.

In the alternative, the concentration of the drug in the packaging solution is greater than the concentration of the drug in the coating layer. In that case, it is likely that the drug in the packaging solution would migrate into the coating layer and eventually reach a steady state equilibrium state, but that need not be the case.

In yet another instance, a drug provided in the packaging layer that is not present in the coating layer may be present. In that case, it is likely that the drug in the packaging solution would migrate into the contact lens and eventually reach a steady state equilibrium state, but that need not be the case.

II. Methods of Making Medical Devices Including a Medicament—in General

The present invention also includes a method of making an article of manufacture, including: a) providing a medical device including at least one surface; b) depositing one or more coatings on at least a portion of the at least one surface, wherein the one or more coatings includes; 1) at least one drug reservoir layer deposited at least in part by printing on the at least one surface, wherein the at least one drug reservoir layer comprises at least one drug.

The present invention also includes a method of making an article of manufacture, including: a) providing a medical device including at least one surface; b) depositing one or more coatings on at least a portion of the at least one surface.

Having discussed the particular structures of the present invention, what they are made of, how they are preferably made, how they interact, how they are assembled and how they are chosen based on their physical and chemical nature, and the like, the discussion now turns to how the article of manufacture is made, with exemplary and preferred examples later provided in the examples section.

Furthermore, U.S. Pat. Nos. 9,931,296 and 10,413,506, all to Doshi generally relate to methods of making medical devices including a medicament, notably methods of making drug delivery contact lenses, and are incorporated by reference herein, notably for the purpose of methods of making medical devices including a medicament, notably methods of making drug delivery contact lenses.

A. Medical Device

First, a medical device is chosen on which a coating is to be provided. Essentially any medical device can be used in the present invention. The choice of the medical device is one within the skill of the ordinary artisan and the state of the art provides vast literature on a wide variety of medical devices and where they are to be implanted and which drugs would be useful to be provided with a coating of the present invention to treat or prevent any number of diseases, conditions or disorders that a subject may suffer from.

The medical device can be implantable or non-implantable as those terms are known in the art and have been previously discussed. In one preferred aspect of the present invention, the medical device includes a cardiac stent or joint replacement apparatus, or other implantable medical device. In another preferred aspect of the present invention, the medical device includes a contact lens or skin patch drug delivery medical device, or other non-implantable medical device.

B. Surface

The medical device presents a surface upon which a coating of the present invention is to be made. The surface of the medical device chosen is usually an inherent property of the medical device, but that need not be the case. The surface can be modified by any number of methods or techniques and known in the art and discussed herein, including chemical modification or physical modification.

In certain preferred aspects of the present invention, as discussed herein, the surface presented for the application of a coating of the present invention includes, but is not limited to, at least one metal, at least one plastic, at least one polymer, at least one partially polymerized polymer, at least one polymer matrix, at least one protein matrix, at least one silicone, at least one ceramic, at least one glass, at least one carbon containing compound, at least one fabric, or a combination thereof.

In other preferred aspects of the present invention, as discussed herein, the surface presented for the application of a coating of the present invention can be modified by a variety of methods before a coating of the present invention is applied thereto. Preferred surface modification methods include but are not limited to one or more chemical processes or one or more physical processes. Preferred chemical processes include, but are not limited to, chemical coating, chemical cleaning, chemical texture modification, chemical or electrochemical activation or creation of reactive groups on or within said at least one surface, application of one or more chemicals to said at least one surface, and combinations thereof. Preferred physical processes include but are not limited to, etching, scoring, spraying of materials on the surface, sputtering of materials on the surface, corona treatment, and combinations thereof.

C. Drug Reservoir Layer

The coating of the present invention includes a drug reservoir layer, which includes at least one drug for later release into or onto a subject at the locus where the medical device is provided to a subject. The drug reservoir layer is preferably provided directly on at least a portion of the surface of a medical device as discussed herein and is the first component of the coating of the present invention. However, at least one layer may be provided before an at least one drug reservoir layer in certain aspects of the invention where the direction of release of a drug from a coating of the present invention is desired, such as the case where a medical device presents multiple surfaces for release of a drug from a coating of the present invention, such as, for example, contact lenses where the drug can be released towards the eye, towards the eyelid, or both.

The drug reservoir layer can be made of any appropriate material or combination of materials, and the choice of material is generally within the skill of the art as influenced by a variety of factors, including but not limited to the printing method to be used to provide the drug reservoir layer, the size, thickness an shape of the drug receiving layer desired, the physical and chemical properties desired for the drug reservoir as influenced by the chemical and physical characteristics of the drug provided in the drug receiving layer such that the drug can be released at a desired rate, and the like.

Preferred materials for the drug receiving layer include, but are not limited to, at least one polymer, at least one partially polymerized polymer, at least one polymer matrix, at least one protein matrix, at least one silicone, at least one ceramic, at least one glass, at least one carbon containing compound, at least one fabric or a combination thereof. Other preferred materials include, but are not limited to, derivatized oligomers, such as but not limited to, HEMA, DMA, GMA, PVA, silicone and siloxane, or combinations thereof.

In certain aspects of the present invention, during the printing process used to make the drug reservoir layer, a non-polymerized or partially polymerized printing formulation, which can include at least one drug, is applied to the surface. In that instance, the non-polymerized or partially polymerized formulation is to be polymerized or otherwise cured to stabilize the drug receiving layer and, in certain aspects of the invention, serves to entrap or otherwise localize a drug in the drug reservoir layer for later release therefrom. Preferred methods for polymerizing or curing a drug reservoir when needed or desirable include, but not limited to, at least one UV curing or polymerization, at least one thermal curing or polymerization, at least one room temperature curing or polymerization, at least one simultaneous printing and curing or polymerization, at least one e-beam curing or polymerization, or combinations thereof.

In certain aspects of the present invention, the drug reservoir layer is bonded to, permanently bonded to, or is not bonded to the surface. In this instance, reactive groups on the surface or the drug receiving layer may chemically or physically interact to form chemical bonds, such as covalent bonds, or physical bonds, such as short-range interactions, such as but not limited to hydrogen bonds, van der Walls interactions, hydrophobic interactions, hydrophilic interactions, ionic interactions and the like. The formation of these chemical or physical interactions is dependent upon the chemical nature of the surface and the drug reservoir layer and can be determined by the artisan based on based on the state of the art.

In another aspect of the present invention, as discussed herein, the drug receiving layer can release a drug in one or more directions. In certain cases, the drug receiving layer, based on the nature of the medical device and surface, can release a drug only in one direction as the surface will prevent, or block, the release of drug in one direction as the drug is not able to substantially migrate into the surface or medical devices based on the material presented. As discussed herein, a blocking layer may be provided to prevent a drug from migrating in one direction. As discussed herein, a drug may be released in more than one direction, such as the case of contact lenses.

D. Drug Receiving Layer

In one aspect of the present invention, the at least one drug reservoir includes an at least one drug receiving layer. In this aspect of the present invention, the drug receiving layer is printed on the surface, as the drug reservoir layer with at least one drug is as described herein, and an at least one drug is provided to said at least one drug receiving layer to form a drug reservoir layer. The drug is provided to the drug receiving layer my any appropriate method, such as by printing as described herein, but other methods of proving a drug to a drug receiving layer can be used, such as, but not limited to, soaking, dipping and spin coating. As with other layers of the coating of the present invention, the drug receiving layer can be made of any appropriate material or combination of materials, and the choice of material is generally within the skill of the art as influenced by a variety of factors, including but not limited to the printing method to be used to provide the drug receiving layer, the size, thickness an shape of the drug receiving layer desired, the physical and chemical properties desired for the drug reservoir as influenced by the chemical and physical characteristics of the drug provided in the drug receiving layer such that the drug can be released at a desired rate, and the like.

In one aspect of the present invention, the at least one drug reservoir layer includes a chemical coating applied to the surface. In the alternative, the at least one drug receiving layer is applied to another layer that has been previously applied to the surface, such as, but not limited to, a layer to produce a coating layer that released a drug in a particular directions from the coating as described herein.

In another aspect of the present invention, the printing formulation used to print the drug receiving layer can include materials, such as chemicals, to allow for the polymerization or curing of the printed drug reservoir layer, and in certain instances, to allow for the tailoring of the physical characteristics of the drug receiving layer that affect the release of the drug therefrom as described herein, such as, but not limited to porosity, diffusion rate of a drug, and the like. The materials used to obtain these objectives include, but are not limited to bonding agents, cross linking agents, or a combination thereof. The use of bonding agents, cross linking agents, or combinations thereof to provide materials with desirable physical characteristics for the present invention are known in the art and are replete in the literature and adaptation to the present invention can be made using experimentation or mathematical modeling.

In one preferred aspect of the present invention, the drug receiving layer includes a highly absorbent polymer. Preferred highly absorbent polymers include, but are not limited to, at least one polyvinylpyrrolidine homopolymer, at least one polyvinylpyrrolidone copolymer, at least one polyacrylamide homopolymer, at least one polyacrylamide copolymer, at least one polyacrylate homopolymer, at least one polyacrylate copolymer, at least one proteinaceous material, at least one carbohydrate, or a combination thereof.

The drug reservoir can be applied to a surface or desired location using any appropriate method or means as described herein or as known in the art. Preferred methods or means include but are not limited to, direct coating, application of droplets or microdroplets, ink jet printing, soaking, impregnation, spin coating, drip coating, screen coating, silk screen coating, pad printing, or a combination thereof.

E. Drug

As discussed previously, the at least one drug reservoir layer of the at least one coating of the present invention includes at least one drug provided therein such that the at least one drug can be released from the at least one coating. In general, the choice of drugs to be provided in the coating layer are a matter of choice for the artisan, and there is a vast body of literature, both patent and not patent, available to the artisan to identify drugs that are effective to treat or prevent an disease, disorder or condition.

The drug can be provided in the coating in an amount sufficient such that when the drug is released from the coating it is provided in a therapeutically effective amount for the route of administration and location of the medical device of the present invention within or on the subject. The physical characteristics of the coating of the present invention as discussed herein, such as, but not limited to, pore size and water content, can be taken into account when considering what concentration of drug to be provided in the coating of the present invention such that the appropriate amount of drug is released from the coating of the present invention.

As discussed herein, a medical device of the present invention is provided within or on a subject such that the drug is released at a particular locus rather than systemically as with other drug delivery methods, such as through injection or oral administration. This allows for the drug to be delivered at a particular location and preferably at a lower or more precise dose than would otherwise be obtainable. The focused delivery of a drug by the medical device of the present invention also would reduce the instance of side effects of drugs that more systemic routs of administration would be characterized because the total body load of a drug in a subject would be greatly reduced compared to more systemic administration of a drug.

As discussed herein, the location of the drug delivery device is determinable by the nature of the medical device and the disease, disorder or condition to be prevented or treated. For example, implantable cardiac stents would be provided in blood vessels as is the normal course of treatment, and contact lenses would normally be provided on the eye, but this need not be the case.

The drug can be provided with the coating layer of the present invention or released from the coating layer of the present invention in a variety of forms. In one aspect of the present invention, the drug is provided in the coating layer or released from the coating layer at least in part as a sole active ingredient without any other ingredient association that can alter the activity or deliverability of said at least one drug. That is to say, the drug is provided or released in a free state and not associated with other chemical entities, such as drug delivery chemical entities as described herein or known in the art.

In the alternative, the drug is provided in the coating layer or released from the coating layer at least in part in at least one encapsulated form, at least one micro-encapsulated form, at least one nano-encapsulated form, in at least one emulsion, in at least one water-in-oil emulsion, in at least one oil-in-water emulsion, or in at least one liposome, or a combination thereof, as described herein or as known in the art.

As described herein the drug provided in the coating layer or released therefrom can be virtually any drug, including but not limited to small molecule drugs or biological drugs as they are known in the art. There is a vast body of literature, both patent literature and non-patent literature for these types of drugs. A comprehensive list is beyond the scope of this document. Preferred classes of drugs are provided herein, and include, but are not limited to, at least one anti-inflammatory drug, at least one anti-allergy drug, at least one antibiotic drug, at least one drug for the treatment of glaucoma, at least one drug for the treatment of macular degeneration, at least one ophthalmic drug, at least one hydrophilic drug, at least one hydrophobic drug, at least one anti-parasitic drug, at least one steroid drug, at least one medicament for the treatment of dry eye and at least one medicament for treatment of eye discomfort, or a combination thereof.

In one preferred aspect of the present invention, the drug is provided in a coating layer or released from the coating layer in an at least one encapsulated form. Preferred encapsulation materials are discussed herein and are known in the art, and include, but are not limited to at least one biodegradable polycyanoacrylate, at least one biodegradable poly(alkylcyanoacrylates), at least one biodegradable calcium phosphate, at least one legumin, at least one polysaccharides drafted with polyesters (amphyphilic copolymers), at least one poly(methylidene malonate), at least one gelatin, at least one poly(E-caprolactone), at least one sodium alginate, at least one agarose hydrogel, at least one PMMA, at least one biotinylated poly(ethylene glycol) conjugated with lactobionic acid, at least one poly(vinyl alcohol) hydrogel, at least one biotinylated pullulan acetate, at least one dibloc copolymers and combinations thereof.

In another preferred aspect of the present invention, the polycyanocrulate are those disclosed herein or known in the art, including but not limited to, at least one polybutylcyanoacrylate, at least one polyhexylcyanoacrylate, at least one polyethyl-cyano-acrylate, at least one polyisobutylcyanoacrylate and combinations thereof.

In one preferred aspect of the present invention, the drug is provided in a coating layer or released from the coating layer in a nanoencapsulated form with a least one encapsulation material in nanoparticles, a least one oil-in-water emulsion, at least one water-in-oil emulsion or at least one liposome material, or a combination thereof. The nanoparticles, when present, can be any disclosed herein or described in the art, including but not limited to, chitosan nanoparticle, human serum albumin nanoparticle; silica nanospheres, PEG'ylated core-shell nanoparticles, biodegradable PGGA (poly(D,L-lactide-co-glycolide) particles, PLA (poly lactic acid), PGA, PLG (poly-(D,L-glycolide) polymeric nanoparticles, biocompatible gliadin nanoparticles, low pH sensitive PEG stabilized plasmid-lipid nanoparticles, tocopherol derivatives stabilized nano-sized emulsion particles, PLA-PEG nanoparticles, nanoparticles composed of hydrophilic proteins coupled with apolipoprotein E, biodegradable poly(vesiln-caprolactone) nanoparticles, biotinylated poly(ethylene glycol) conjugated with lactobionic acid, carboxylmethyl dextran magnetic nanoparticles and combinations thereof.

F. Printing

One aspect of the present invention is that the various components of the at least one coating are preferable made using at least one printing technology. The components of the coating include, but are not limited a variety of layers, including but not limited to, and may not include all of the listed components, at least one drug reservoir layer, at least one drug receiving layer, and at least one layer. The same or different printing technologies can be used to make the various components. Likewise, one or more printing technologies can be used to make a particular component. The printing of the various components, or layers, preferably uses a printing formulation of the present invention, but that need not be the case. Printing formations of the present invention are described in further detail herein.

A wide variety of printing technologies are applicable to providing the various layers of the coating of the present invention. The choice of which printing technology to use is a matter of choice for the skilled artisan based on the particular size, shape, thickness, printing resolution and other characteristics of the layer being provided. One skilled in the art would have available technical literature to match the desired characteristics of the layer to be printed with the characteristics, benefits and limitations of a printing technology. Likewise, one skilled in the art would be able to match a printing formation used to make a layer of the present invention with a particular printing technology, and the desired characteristics of the layer to be printed as well.

The characteristics of the printing formulation being used to make the layer, such as, but not limited to the viscosity and surface tension of the printing formation. Also, the nature of the printing device in combination with the printing formation is a factor to consider, such as the case when a printing technology, such as but not limited to ink jet printing technology utilize printing structures that may require relatively stringent physical and chemical characteristics of the printing solution such that the printing formulation does not clog or otherwise damage or interfere with the printing device.

In addition, as some of the layers are printed in liquid or semi-solid form and then transformed into a solid or semi-solid form by, for example but not limited to polymerization or partial polymerization, the characteristics of the printing liquid or semi-solid is to be taken into account. As a preferred aspect of the present invention, the compositions of Doshi et al., published U.S. application No. 2008/0062381A1, published Mar. 13, 2008, are applicable, particularly when the pigment is optionally present in such formulations, and at least one drug is optionally provided in such formulations.

Preferred printing methods are digital in nature, such as those described by Doshi et al. (U.S. 2008/0062381A1) which is incorporated by reference herein in its entirety, such that they allow for a relatively highly precise method and means to provide a high quality and well defined print product. As the method and associated device are digital in nature, the printing process is adaptable for computer control and product design. Preferred digital printing methods and structures are discussed herein. As a non-limiting introduction to digital printing methods and devices, the following digital printing methods are preferred: ink jet printing, three dimensional printing (3D printing), piezo printing, thermal printing, laser printing MEMS printing, wherein the printing head or related or associated structures are rotatable or non-rotatable. Generally, but not exclusively, a printing solution of the present invention replaces the ink solution of existing and commercially available printing devices, in particular within the printing cartridge.

Likewise, preferred printing methods include pad printing as those methods are known in the art, including but not limited to pad transfer printing. Pad printing is not as exact as digital printing but is a preferred method of printing for the present invention. Pad printing is known in the art for printing of images of the iris of the eye on contact lenses (see, U.S. Pat. Nos. 5,414,477, 5,302, 978, and 4,668,240).

Ink jet printing is known in the art and can take various forms and associated structures as are discussed herein. Generally, ink jet printing refers to printing devices and methods that utilize highly precise printing methods and structures that allow for the production of high quality and precise structures. Generally, available ink jet printing devices and structures can be utilized with minimal modification, with the ink solutions normally present in the ink jet cartridge or reservoir is replaced with a solution that includes a polymerizable monomer and associated polymerization initiators as needed. The polymerizable monomer can be polymerized at will and at a rapid rate after being dispensed from the ink jet printing structure.

Three dimensional printing is based primarily, but not exclusively, on ink jet printing technologies. These methods and devices allow for the generation of one-off or multiple copies of a structure or structures. Generally, a polymerizable solutions is placed within the printing device and is dispensed under computer control and polymerized in repeated printing cycles or steps to generate a three dimensional structure. Examples of available and preferred 3D printing devices and related structures and cartridges include, but are not limited to: 3D Systems (www.3dsystems.com/default.asp) (Mar. 29, 2011), ProJet™ 6000 Professional 3D Printer (http://printin3d.com/sites/printin3d.com/files/downloads/Projet_6000_brochure_USEN.pdf) (Mar. 29, 2011); Stratasys, Inc. (http://www.stratasys.com/); Fortus 3D Production Systems—Fortus 900mc; Z Corporation (www.zcorp.com); Zprinter® 650 (http://www.zcorp.com/en/Products/3D-Printers/ZPrinter-650/spage.aspx)Vertical Resolution—90 to 100 microns (0.0035 to 0.004 in) Smallest Feature—100 microns (0.004 in); 3D Systems (http://www.3dsystems.com/default.asp); and Viper si2™ SLA® System http://www.3dsystems.com/products/datafiles/viper/datasheets/Viper_final_rev_0303.pdf.

Piezo printing is a subtype of ink jet printing that is a preferable printing method of the present invention. Examples of available and preferred piezo printing devices and related structures and cartridges include, but are not limited to: MicroFab Technologies, Inc. (www.microfab.com) (Mar. 29, 2011); Jetlab® 4xl, 4xl-A ((http://www.microfab.com/equipment/pdf/jetlab4xl_xla.pdf) (Mar. 29, 2011); X-Y Accuracy/Repeatability—+/−25 microns/+/−5 microns (4xl-A); O.N.E Technologies (www.onelabs.com) (Mar. 29, 2011); Material Deposition Systems (www.onelabs.com/matdep00.htm) (Mar. 29, 2011), Resolution as low as 0.2 nanometer; Multi-Axis Printing Systems (www.onelabs.com/maxp00.htm) (Mar. 29, 2011); FujiFilm USA | Dimatix, Inc. (http://www.dimatix.com/index.asp) (Mar. 29, 2011); Dimatix Materials Printer DMP-5000 (http://www.dimatix.com/files/DMP-5000-Datasheet.pdf) (Mar. 29, 2011) X-Y Accuracy/Repeatability—+/−5 microns/+/−1 microns; Mimaki JF Series (http://www.mimakiusa.com) (Apr. 1, 2011) Model JF1610 or JF 1631 (http://www.mimakiusa.com/IndustrialProduct.aspx?level=3&pid=3&cid=14) (Apr. 1, 2011), resolution up to 1200 by 1200 dpi.

Thermal printing is a subtype of ink jet printing that is a preferable printing method of the present invention. Examples of thermal printing devices and related structures and cartridges include, but are not limited to: Hewlett Packard (www.hp.com) (Apr. 1, 2011); HP Designjet H45000 Printer Series http://www.hp.com/united-states/colorspan/djh45000-datasheet.pdf (Apr. 1, 2011).

Laser printing is a subtype of ink jet printing that is a preferable printing method of the present invention. Examples of laser printing devices and related structures and cartridges include, but are not limited to those known in the art such as Xerox Phaser 6010 laser printer http://www.xerox.ca/office/printers/colour-printers/phaser-6010/spec-enca.html or HP Color LaserJet Enterprise CP4025 Printer series—HP Color LaserJet Enterprise CP4025dn Printer (CC490A) http://h10010.www1.hp.com/wwpc/us/en/sm/WF06b/18972-18972-3328060-15077-236268-3965792-3965795-3974244.html, or those later developed.

Optionally, a printing device, such as but not limited to an ink jet printing device, can include a rotating printer head. These types of printing structure can allow for enhanced printing on curved surfaces. Preferably, doughnut shapes can be printed on a contact lens such that the visible light transmission of the optical center of the lens is not affected.

Another preferred printing method is MEMS printing is based on technologies that allow for the printing of integrated circuit boards, but are applicable to the production of very small structures that have functionality. Examples of structures having functionality made by MEMS printing include mechanical gears and other mechanical devices, lab on a chip structures for the performance of laboratory procedures including chemical reactions and diagnostic procedures.

Another preferred printing method is MEMS printing and is based on technologies that allow for the printing of integrated circuit boards, but are applicable to the production of very small structures that have functionality. Examples of structures having functionality made by MEMS printing include mechanical gears and other mechanical devices, lab on a chip structures for the performance of laboratory procedures including chemical reactions and diagnostic procedures.

G. Printable Formulation

Printable formulations useful in the present invention for printing of layers or structures of the present invention using printing technologies as discussed herein and known in the art, particularly digital printing methods and technologies, can optionally include one or more drugs, any single drug compound or composition, or any combination of drug compounds or compositions. Printable formulations can be provided in water, monomer or solvents, preferably at a concentration between about 0% and greater than about 99.5% or between about 0.001% and about 99.5%, preferably between about 0.005% and about 90% or between about 1% and about 80%, and more preferably between about 10% and about 60% or between about 20% and about 40%. Printable formulations can also include particles or particulates, preferably at a concentration of between about 0% and about 15% or between about 0.001% and about 10%, preferably between about 0.005% and about 4% or between about 1% and about 3% to render a digitally printed formulation optionally with at least one drug. Examples of drugs include, but are not limited to, Timolol, Gentamycin and Nevanac. As discussed herein, the characteristics and compositions including printable formulations and other components include printable formulations that are or become part of an article of manufacture of the present invention, such as a lens, such as a contact lens, and also include compositions that include at least one printable formulations that can be used to make any article of manufacture of the present invention.

Printable formulations can include water, monomer, polymer or an appropriate solvent in order for the printable formulations to be suitable in the making of a digital print. An appropriate solvent is a solvent that is compatible with the creation of a print such as a digital print on or within a surface, such as on or within a polymer. For example, solvents appropriate for polymers used to make lenses, such as contact lenses, include, but are not limited to isopropanol, water, acetone or methanol, either alone or in combination and can include a monomer. Appropriate concentrations of solvents are between about 0% and greater than about 99.5% or between about 0.1% and about 99.5%, preferably between about 1% and about 90% or between about 10% and about 80%, and more preferably between about 20% and about 70% or between about 30% and about 60%. Different polymers, monomers and printable formulations have different tolerances and reactivity to different solvents. Thus, appropriate matches between solvent and polymer, monomer and printable formulations can be considered. For hydrogel polymers, adjustment in swelling ratios may be achieved with a variety of concentrations of solvents or crosslinkers.

A printable formulation can also include a monomer, polymer, homopolymer, heteropolymer, or copolymer. In a preferred aspect of this aspect of the present invention, a printable formulation includes a monomer that can be polymerized to form a polymer using polymerization methods appropriate for a given monomer, mixtures thereof, or polymers, or mixtures thereof. Monomers can also be used to decrease the viscosity of the printable formulation. Alternatively, the printable formulation can include a polymer such that the viscosity of the printable formulation is increased. Alternatively, the printable formulation can include polymer and monomer. Appropriate concentrations of monomers are between about 5% and greater than 99%, preferably between about 25% and about 75%, and more preferably between about 35% and about 60%. Appropriate concentrations of polymers are between about 0% and about 50%, preferably between about 5% and about 25%, and more preferably between about 10% and about 20%. When monomers and polymers are mixed, the total concentration of monomer and polymer are between about 10% and greater than 99%, preferably between about 25% and about 75% and more preferably between about 35% and about 65%.

The viscosity of a solution including a printable formulation can be as high as between about 500 centipoise and about 5,000 centipoise and is preferably between about 1 to about 200 centipoise or between about 10 and about 80 centipoise, preferably between about 20 and about 70 centipoise or between about 30 and about 60 centipoise or between about 1 and about 10 centipoise. Solutions having low viscosity tend to be "runny" when dispensed, and can allow different colors to merge and blend, resulting in an image with a more natural appearance. Such blending can be enhanced using a variety of methods, including sonication or vibration at appropriate duration and frequency to promote appropriate blending. Solutions having too low a viscosity can result in images that are too "runny" and thus have potentially undesirable characteristics, such as pooling of a printable formulation in a digitally encoded image or spreading of a printable formulation to an unintended location. Solutions having too high a viscosity may be easily dispensed using pad printing but are not suitable for other printing. Furthermore, solutions having high viscosity can tend to "bead" on a surface and not blend with the surrounding environment, including surrounding droplets or beads of printing formulation. Agents such as thickeners or diluents (including appropriate solvents) can be used to adjust the viscosity of the printable formulation.

Alternatively, one may use drug receiving layer that holds inkjetted digital droplets in its place until fixed. Another approach can be to use printable formulations that uses derivatized oligomer to be able to stop it from running by instant curing. Both of these approaches are discussed herein.

A printable formulation that includes at least one monomer can also include a polymerization initiator, so that once a printable formulation that includes at least one type of monomer is dispensed, the polymerization of the monomer in the printable formulation is initiated. The number, type and amount of initiator is a matter of choice depending on the type of monomer or monomers in the printable formulation. Appropriate initiators include, but are not limited to, UV initiators that initiate polymerization by UV irradiation, thermal initiators that initiate polymerization by thermal energy.

A printable formulation can also include a dispersant to allow uniform composition of formulation in a container. Dispersants are preferably provided at an appropriate concentration, such as between about 1% and about 10%.

A printable formulation can also include at least one anti-microbial agent or antiseptic agent to kill or reduce the number or multiplication microbial agents, reduce the number of microbial agents, or keep microbial agents from multiplying. Preferred anti-microbial agents include anti-bacterial agents, anti-fungal agents and disinfectants. Preferably, such anti-microbial agents, anti-bacterial agents, anti-fungal agents and disinfectants are provided at an appropriate concentration such as between about 0% and about 1%.

A printable formulation can also include at least one humectant such as 1,3-diozane-5,5-dimethanol (U.S. Pat. No. 5,389,132) at an appropriate concentration. Preferably, the range of concentration of a humectant is between about 0% and about 2%.

A printable formulation can also include at least one antioxidant agent or a low corrosion agent, such as alkylated hydroquinone, at an appropriate concentration, such as between about 0.1% and about 1% (U.S. Pat. No. 4,793,264). A PF can also include a non-kogating agent or non-kogating agent, such as 2-methyl-1,3-propanediol at an appropriate concentration, such as between about 0% and about 1%. A printable formulation can also include an evaporation retarding agent, such as, for example, diethylene glycerol or ethylene glycol at between about 0% and about 2% (U.S. Pat. No. 5,389,132).

A preferred printable formulation can have the following composition:

| Component | Percentage |
| --- | --- |
| Monomer | 0% to 99% |
| Drug or Encapsulated Drug | 0% to 25% |
| Initiator | 0.01% to 2% |
| Solvent | 0% to 80% |
| Binder or Bonding Agent | 0% to 10% |
| Thickener | 0% to 1% |
| Anti-kogating Agent | 0% to 1% |
| Humectant | 0% to 1% |
| Surfactant | 0% to 10% |
| Cross-linker | 0% to 1% |
| Dispersant | 0% to 10% |

H. Modulation of Release of Drug

As previously discussed, the combination of the layers and components of the coating of the present invention serve to modulate the release of at least one drug from the coating.

A variety of physical and chemical forces influence the modulation of the release of a drug from a coating of the present invention. These include, but are not limited to diffusion characteristics of at least one layer of a coating of the present invention or the coating itself, capillary action characteristics of at least one layer of a coating of the present invention or the coating itself, mass action characteristics of at least one layer of a coating of the present invention or the coating itself, concentration gradient of a drug in at least one layer of a coating of the present invention or the coating itself, solubility of a drug characteristics of at least one layer in a coating of the present invention or the coating itself, temperature, molecular weight of a drug, size of a drug, encapsulation structures for a drug, thickness of at least one layer of a coating of the present invention or the coating itself, porosity of at least one layer of a coating of the present invention or the coating itself, the pore size of at least one layer of a coating of the present invention or the coating itself, the molecular exclusion size or characteristics of at least one layer of a coating of the present invention or the coating itself, the water content of at least one layer of the coating of the present invention or the coating itself, the concentration of a drug in at least one layer of a coating of the present invention or the coating itself, the concentration gradient of a drug in at least one layer of a coating of the present invention or the coating itself, and the packaging environment presented to the coating of the present invention.

In one aspect of the present invention, the at least one drug has sustained release over time. In another aspect of the present invention, the at least one drug has intermittent release over time. In yet another aspect of the present invention, more than one drug is released at a time.

I. Contact Lens

In one preferred aspect of the present invention, the medical device having a coating being made includes a contact lens. Contact lenses that include a drug, on the surface of the contact lens or within the contact lens are known in the art. However, these contact lenses do not provide the structures of the present invention, such as the at least one coating that includes at least one drug reservoir layer that can include at least one drug, and at least one layer that can include structures, wherein the release of the at least one drug from the at least one coating layer is modulated by at least one layer of the coating of the present, either alone or in combination.

The choice of printing technologies used to make the various layers of the coating of the present invention, including the coating layer as a whole, is a choice for the artisan based on the state of the art and the teachings provided herein, as well as an evaluation of the various factors to consider when choosing a printing technology to produce a structure having desired chemical and physical properties, along with a consideration of the printing formation to be used.

A variety of materials are known in the art for making contact lenses and are useful in the present invention. Preferred materials include, but are not limited to, acrylics, silicones, polyvinylalcohols, and combinations thereof. These materials are provided on the surface of the contact lens to be modified using the methods of the present invention.

There are a variety of general types of contact lenses known in the art and are useful in the present invention. Preferred general types of contact lenses include, but are not limited to hybrid lenses, hydrophilic lenses and hydrophilic lenses. These types of contact lenses provide a surface of the contact lens to be modified using the methods of the present invention.

In addition, there are other general types of contact lenses known in the art and are useful in the present invention. These lenses include, but are not limited to spherical lenses, toric lenses, multifocal lenses, tinted lenses, corrective optical power lenses and lenses without corrective optical power. These types of contact lenses provide a surface of the contact lens to be modified using the methods of the present invention There are a variety of methods used to make lenses that are useful in the present invention. Preferred methods of making, at least in part or in combination, contact lenses include, but are not limited to, lathing, cast molding, spin casting and ink jet printing. These contact lenses provide a surface of the contact lens to be modified using the methods of the present invention.

Once a contact lens is manufactured, a variety of secondary or finishing operations can be utilized and are useful in the present invention. Preferred secondary or finishing operations include, but are not limited to edging, polishing, tinting, hydration, extraction, and sterilization. These secondary or finishing operations can optionally take place before or after the contact lens is modified by a method of the present invention, or both.

In one aspect of the present invention, the at least one drug in an at least one coating layer can be provided on the surface of a contact lens. In another aspect of the present invention, the at least one drug in at least one coating layer can be provided within a contact lens. In another aspect of the present invention, the at least one drug can be provided inside a contact lens without the structures in an at least one coating layer in combination with at least one drug in at least one coating layer on the surface of a lens. In yet another aspect of the present invention, the at least one coating layer with at least one drug can be provided both on the surface of the lens and inside the lens.

In some cases, drugs provided within the at least one coating can have optical properties that can interfere with the optical function of the contact lens, such as drugs having coloring or opaqueness. Preferred drugs for use in the present invention do not have such optical properties, but that need not be the case as drugs having such optical properties are useful in the present invention.

In another aspect of the present invention, the one or more coatings can optionally dispersed therein nanoparticles having a particles size less than about 50 nm, a nanoencapsulated ophthalmic drug from which the ophthalmic drug is able to diffuse into and migration through the contact lens and into the post-lens tear film or towards the eyelid when the contact lens is placed on the eye, the nanoparticles being disperse within the contact lens or on at least one surface of the contact lens in an amount such that the lens optionally remains substantially optically transparent (see, for example, U.S. Pat. No. 7,638,137B2 to Chauhan et al., issued Dec. 29, 2009).

In another aspect of the present invention, the one or more coatings can optionally dispersed therein nanoparticles having a particles size less than about 50 nm, a nanoencapsulated ophthalmic drug from which the ophthalmic drug is able to diffuse away from and migrate away from the contact lens and into the post-lens tear film or towards the eyelid when the contact lens is placed on the eye, the nanoparticles being disperse within the contact lens or on at least one surface of the contact lens in an amount such that the lens optionally remains substantially optically transparent (see, for example, U.S. Pat. No. 7,638,137B2 to Chauhan et al., issued Dec. 29, 2009).

In yet another aspect of the present invention, when the at least one drug is provided with or without a drug delivery compositions as described herein, the at least one drug as provided with or without a drug delivery compositions is substantially optically transparent. However, this need not be the case. In one aspect of the present invention, when the at least one drug as provided with or without a drug delivery composition is substantially optically transparent or is not substantially optically transparent, the optical characteristics of the at least one drug, or other structures of the at least one coating layer, can be masked with opaque material or tinting, such as color tinting as is known in the art.

J. Packaging

An article of manufacture made by a method of the present invention can be provided in a variety for forms and packaging formats and solutions as present. Many of these packaging form and formats are established packaging formats, whereas others are unique to the present invention.

The article of manufacture made by a method of the present invention can be provided in a packaging in a dry state, preferably in a dehydrated state or a lyophilized state using methods know in the art. The article of manufacture made by a method of the present invention can also be provided in a packaging in a wet state, that is to say provided in an appropriate solution and, as appropriate, in a hydrated state.

The format of the packaging can be any as is appropriate. For example, the article of manufacture made by a method of the present invention can be provided in packaging that is appropriate and normal for the article of manufacture, such as vials, other containers such as boxes or plastic containers, or in vials. Vials and blister packaging are preferable, but not necessary, for example, for contact lenses.

The solution present, if any, in a packaging format, in particular for a wet state packaging format can include the at least one drug present in the at least one coating layer, a different drug that that provided in the coating layer, or a combination thereof.

In one instance, the concentration of the drug in a packaging solution is less than the concentration of the drug in the coating layer. In that case, it is likely that the drug in the coating layer may migrate from the coating layer into the packaging layer and eventually reach a steady state equilibrium state, but that not be the case.

In another instance, the concentration of the drug in a packaging solution is equal to the concentration of the drug in the coating layer. In that case, it is likely that the drug in the packaging solution will be in steady state with the drug in the coating layer, but that need not be the case.

In the alternative, the concentration of the drug in the packaging solution is greater than the concentration of the drug in the coating layer. In that case, it is likely that the drug in the packaging solution would migrate into the coating layer and eventually reach a steady state equilibrium state, but that need not be the case.

In yet another instance, a drug provided in the packaging layer that is not present in the coating layer may be present. In that case, it is likely that the drug in the packaging solution would migrate into the contact lens and eventually reaches a steady state equilibrium state, but that need not be the case.

III. Methods of Using Lenses Including a Medicament—in General

The present invention includes method of treating or preventing a disease, disorder or condition or condition including: a) providing a subject in need of treatment of said disease, disorder or condition; and b) providing the subject the article of manufacture of the present invention, optionally made using the methods of the present invention, at a location appropriate for the treatment of said disease, disorder or condition; wherein the article of manufacture releases the one or more drugs in an amount sufficient to treat or prevent said disease, disorder or condition.

Furthermore, U.S. Pat. Nos. 9,931,296 and 10,413,506, all to Doshi generally relate to methods of using medical devices including a medicament, notably methods of using drug delivery contact lenses, and are incorporated by reference herein, notably for the purpose of methods of using medical devices including a medicament, notably methods of using drug delivery contact lenses.

The article of manufacture of the present invention, its components and a compositions along with their desirable characteristics and selection criteria, how they are arranged and function together, and what criteria can be utilized to select and arrange them for a particular article of manufacture for a particular purpose, have been described herein. In addition, the methods of manufacture of the article of manufacture of the present invention, along with the manufacture of the coating layer and its various components, including but not limited to the drug reservoir layer, and the drug receiving layer, along with the printing formulations and printing technologies used to make them and the physical characteristics of the modulation of drug release therefrom, along with the criteria for selecting them for the manufacture of an article of manufacture for a particular purpose have also been described herein. The criteria for the selection of a drug, including for what purpose it is to be used for, its physical characteristics, its concentration, release characteristics and modulation thereof, have also been described herein.

An article of manufacture of the present invention, optionally made by a method of the present invention, tailored for the treatment or prevention of a particular disease, disorder or condition, and the drug has been selected and provided for in the article of manufacture such that the release characteristics have been evaluated based on the desired dose, regime, route of administration and locus of administration, and the pharmacological characteristics of the drug is provided. The drug has preferably been selected to match the disease, disorder or condition at hand, along with the locus at which it is released based on the criteria disclosed herein and provided by the state of the art.

A subject in need of treatment or prevention of a disease disorder or condition is also provided. The article of manufacture is then place on or within the subject at a desirable location using methods known in the art based on the locus at which the article of manufacture of the present invention is place (such as, but not limited, insertion on a surface, insertion, or implantation, inclusive of surgery if called for) such that the drug is released from the article of manufacture to treat or prevent a disease, disorder or condition. When the drug has been released over time, the article of manufacture can be removed from the subject, or in the alternative, removed from the subject. In the case of an article of manufacture of the present invention that has been placed on readily accessible locus of a subject, such as the skin or eye, the removal is readily performed. In the case of articles of manufacture of the present invention that have been implanted or inserted into a subject, the removal process is more complex and may require surgery. In some instances, removal of an article of manufacture of the present invention from a subject is not desirable due to the discomfort or risk associated with the removal. In that instance, the article of manufacture can remain in place.

IV. Packaged Medical Device that Includes a Drug Delivery Contact Lens

The present invention includes a packaged medical device, including: a) at least one drug delivery contact lens, including: 1) at least one coating provided on at least one surface of the drug delivery contact lens; 2) at least one hydrophobic drug in at least one oil-water microemulsion; wherein the at least one coating includes the at least one hydrophobic drug; further wherein the at least one coating is made in whole or in part by additive printing; b) at least one packaging solution, including: 1) said at least one hydrophobic drug; 2) at least one cyclodextrin, at least one oil-water microemulsion, or a combination thereof; c) at least one packaging, including: 1) the at least one drug delivery contact lens; and 2) the at least one packaging solution; d) wherein the oil-water microemulsion in the drug delivery contact lens optionally includes at least one cyclodextrin; e) further wherein said hydrophobic drug is stabilized in the drug delivery contact lens, in the packaging solution, or a combination thereof.

The present invention can be practiced using the materials and methods and the like disclosed herein, or as are known in the state of the art or later developed.

A. Drug Delivery Contact Lens

An aspect of the present invention, the drug delivery contact lens includes: a) a soft contact lens; b) a multifocal contact lens; or c) a combination thereof.

B. Modulating Drug Release

An aspect of the present invention includes wherein the release of the at least one hydrophobic drug from the drug delivery contact lens is modulated by the physical properties of the drug delivery lens, the chemical properties of said drug delivery lens, or a combination thereof.

Another aspect of the present invention includes wherein the physical properties of the drug delivery lens include structures or conditions provided by the additive printing, or a combination thereof.

A further aspect of the present invention includes wherein the chemical properties of the drug delivery lens include chemical compounds, chemical compositions, oil-water microemulsions, or short-range interactions or a combination thereof.

An additional aspect of the present invention includes wherein the chemical properties of the drug delivery contact lens are modified by the addition of at least one cyclodextrin to change the rate at which drug is released from said drug delivery contact lens.

C. Coating

An aspect of the present invention includes wherein the at least one coating includes one or more layers.

D. Hydrophobic Drug

An aspect of the present invention includes wherein the at least one hydrophobic drug is provided in a pharmaceutically effective amount.

Another aspect of the present invention includes wherein the at least one hydrophobic drug includes a prostaglandin, a prostaglandin derivative, latanoprost, bimatoprost, atropine, a cannabinoid that can treat glaucoma, a THC, or a combination thereof.

Endogenous and exogenous cannabinoids are useful for treating glaucoma and other diseases, disorders, and conditions of the eye, such as those treatable by their neuroprotective effect. Inter ocular pressure (TOP) can be altered through the endocannabinoid system (ECS), which is integrated throughout the eye. Two appropriate endocannabinoids are 2-AG and AEA, whose precursor is arachidonic acid. These cannabinoids bind at the cannabinoid receptor 1 (CB1) and compounds that bind CB2 are also useful. Research has demonstrated the medicinal nature of cannabinoids in the reduction of IOP for treatment of glaucoma. Among the cited exogenous compounds introduced are delta-9-tetrahydrocannabinol (delta 9-TH-IC), a phytocannabinoid, delta 8-THC, and WIN 55,212-2, a CB1 agonist. Other endogenous and exogenous cannabinoid and THC's are also effective to treat glaucoma and other conditions of the eye and can have neuroprotective effects. See generally: Panahi Y, Manayi A, Nikan M, Vazirian M. The arguments for and against cannabinoids application in glaucomatous retinopathy. Biomed Pharmacother. 2017; 86:620-627; https://eyewiki.aao.org/Cannabinoids_for_Glaucoma; and Cannabinoids for Glaucoma—EyeWiki (aao.org); and Passani et al. J Clin Med. 2020 December; 9(12): 3978. Extracts of *cannabis* in crude, partially purified form, purified form, and pure compounds, or mixtures thereof, are also useful for treating diseases, disorders, and conditions of the eye.

A further aspect of the present invention includes wherein the at least one hydrophobic drug is heat labile in aqueous solutions.

An additional aspect of the present invention includes wherein the at least one hydrophobic drug is subject to degradation by hydrolysis.

An aspect of the present invention includes wherein the hydrophobic drug in said drug delivery contact lens, in the packaging solution, or a combination thereof, is steam sterilized, then is heat stabilized, hydrolysis stabilized, or a combination thereof.

E. Oil-Water Microemulsion

An aspect of the present invention includes wherein the at least one oil-water microemulsion includes oil droplets in water medium to form a microemulsion.

F. Printing

An aspect of the present invention includes wherein the additive printing includes ink jet printing.

Another aspect of the present invention includes wherein the additive printing includes digital printing, 3D printing, digital 3D printing, pad printing, or a combination thereof.

A further aspect of the present invention includes wherein the additive printing includes additive printing, additive 3D printing, or a combination thereof.

G. Packaging Solution

An aspect of the present invention includes wherein the packaging solution includes the at least one hydrophobic drug is operably associated with the at least one cyclodextrin, within the at least one oil-water microemulsion, or a combination thereof.

H. Packaging

An aspect of the present invention includes wherein the at least one packaging includes at least one blister pack.

Another aspect of the present invention includes wherein the at least one packaging includes at least one vial.

I. Additional Drugs

An aspect of the present invention includes wherein the at least one drug delivery contact lens, the at least one packaging solution, or a combination thereof, further include at least one additional drug.

Another aspect of the present invention includes wherein the at least one additional drug is provided in a pharmaceutically effective amount.

A further aspect of the present invention includes wherein the at least one additional drug further includes at least one hydrophilic drug.

An additional aspect of the present invention includes wherein the at least one additional drug further includes at least one hydrophobic drug.

An aspect of the present invention includes wherein the at least one additional drug further includes an antibiotic, an intraocular pressure reducing agent, a comfort enhancing agent, an anti-inflammatory agent, a penetration enhancer, a macular degeneration agent, diabatic retinopathy, or a combination thereof.

Another aspect of the present invention includes wherein the at least one additional drug further includes dorzolamide, timolol, or a combination thereof.

A further aspect of the present invention includes wherein the at least one additional drug further includes timolol, alphagan, axopt, cosopt, lumigan, travatan, xalatan, combigan, timolol hemihydrate, betaxolol, levobunolol, metipranolol, apraclonidine, Brimonidine tartate, Brinzolamide, methazolamide, dorzolamide, acetazolamide, carbachol, travoprost, latanoprostene bunod, tafluprost, netarsudil, or a combination thereof.

An additional aspect of the present invention includes wherein the at least one additional drug further includes sodium hyaluronate, hyaluronic acid, cyclosporine, polyethylene glycol 400, hypromellose, polyvinyl alcohol, carboxymethylcellulose, dextran 70, hydroxypropyl methylcellulose, anhydrous liquid lanolin, mineral oil, white petroleum, mannitol, thiomersal, carbomer, cetrimide, glycerin, polysorbate80, povidine, or a combination thereof.

An aspect of the present invention includes wherein the at least one additional drug further includes perdforte, lotemax, fluromethlone, nevanac, acular, xibrom, or a combination thereof.

Another aspect of the present invention includes wherein the at least one additional drug further includes Flurbiprofen, Acetazolamide, ethylenediaminetetraacetic acid, palmitoyl carnitine, sodium caprate, sodium dodecylsulphate, sodium deoxycholate, poly oxyethylene-g-lauryl ether, 1-α-lysophosphatidylocholine, deoxycholate, taurodeoxycholate, glycocholate, benzalkonium chloride, or a combination thereof.

A further aspect of the present invention includes wherein the at least one additional drug further includes Afliberset®.

An additional aspect of the present invention includes wherein the at least one additional drug further includes dexamethasone, at least one steroid, pilocarpine nitrate, tropicamide, methyl prednisolone, flurbiprofen, penicillin, ciprofloxacin, sulphacetaminde sodium, indomethacin, hydrocortisone, indomethacin, ciprofloxacin hydrochloride, insulin, indomethacin, ketorolac tromethamine, or a combination thereof.

An aspect of the present invention includes wherein the at least one additional drug further includes gentamicin, tobramycin, erythromycin, polytrim, cirproflizacin, viamox, xymar, or a combination thereof.

Another aspect of the present invention includes wherein the at least one additional drug further includes atropine.

V. Drug Delivery Contact Lens

The present invention includes a drug delivery contact lens, including: a) at least one coating provided on at least one surface of the drug delivery contact lens; b) at least one hydrophobic drug in at least one oil-water microemulsion; c) optionally at last one cyclodextrin; d) wherein the at least one coating includes the at least one hydrophobic drug; e) further wherein the at least one coating is made in whole or in part by additive printing.

The present invention can be practiced using the materials and methods and the like disclosed herein, or as are known in the state of the art or later developed.

VI. Method of Making Drug Delivery Contact Lens

The present invention includes a method of making a drug delivery contact lens, including: a) providing contact lens; b) printing at least one coating on the contact lens with an ink; 1) wherein the ink includes at least one hydrophobic drug, at least one oil-water microemulsion, or a combination thereof; 2) wherein the ink optionally includes at least one cyclodextrin; 3) wherein the printing includes additive printing; c) wherein the coating, oil-water microemulsion, or a combination thereof, modulates the release of the at least one hydrophobic drug from the drug delivery contact lens, the at least one coating, or a combination thereof.

The present invention can be practiced using the materials and methods and the like disclosed herein, or as are known in the state of the art or later developed.

In an aspect of the present invention, said contact lens comprises a dry hydrogel, silicone, or silicone hydrogel.

VII. Ink

The present invention includes an ink for printing on a contact lens, including: a) at least one monomer; b) at least one cross linker; c) at least one polymerization initiator; d) at least one hydrophobic drug; e) at least one oil-water microemulsion; f) wherein the ink can be used for printing on a contact lens by additive printing.

The present invention can be practiced using the materials and methods and the like disclosed herein, or as are known in the state of the art or later developed.

An aspect of the present invention includes the ink further including at least one cyclodextrin.

VIII. Method of Using a Drug Delivery Contact Lens to Treat or Present a Disease, Disorder, or Condition of the Eve The present invention includes a method of using a drug delivery contact lens, including; a) providing at least one drug delivery contact lens of the present invention that includes at least one hydrophobic drug; b) providing a subject in need of treatment or prevention, or a combination thereof, of at least one disease, disorder, or condition of the eye treatable or preventable, or a combination thereof, by at least one drug in the at least one drug delivery contact lens; c) operably engaging the at least one drug delivery contact lens on the eye of the subject; d) wherein the subject is treated for or prevented from having, or a combination thereof, the at least one disease, disorder, or condition of the eye treatable or preventable, or a combination thereof, by at least one drug in the at least one drug delivery contact lens.

The present invention can be practiced using the materials and methods and the like disclosed herein, or as are known in the state of the art or later developed.

Another aspect of the present invention includes wherein the disease, disorder, or condition of the eye is a) glaucoma; b) myopia; or c) a combination thereof.

The present invention includes a method of treating, preventing, or a combination thereof, at least one disease, disorder, or condition of the eye, including; a) providing at least one drug delivery contact lens of the present invention that includes at least one hydrophobic drug; b) providing a subject in need of treatment or prevention, or a combination thereof, of at least one disease, disorder, or condition of the eye treatable or preventable, or a combination thereof, by at least one drug in the at least one drug delivery contact lens; c) operably engaging the at least one drug delivery contact lens on the eye of the subject; d) wherein the subject is treated for or prevented from having, or a combination thereof, the at least one disease, disorder, or condition of the eye treatable or preventable, or a combination thereof, by at least one drug in the at least one drug delivery contact lens.

The present invention can be practiced using the materials and methods and the like disclosed herein, or as are known in the state of the art or later developed.

EXAMPLES

Example 1: Stabilizing a Latanoprost Packaging Solution

Ophthalmic drugs are traditionally administered via an eyedrop system, which poses several challenges. Firstly, eyedrops have a low bioavailability when applied. The eyedrop typically has a residence time of around 5 minutes or less, which leads to an effective bioavailability of 1-5%. Secondly, eyedrops often suffer from patient non-compliance, a problem that arises from the inconvenience of administering eyedrops, especially more than once a day. Finally, eyedrops generally contain a preservative like benzalkonium chloride, which causes irritation to the eye, further exacerbating the second issue. Several approaches have been proposed to eliminate the use of eyedrops, such as an ophthalmic drug ring, or an implant like Durysta. Another approach is drug delivery via contact lens. By layering an ophthalmic drug into a coating, the "ink", and then applying the coating via inkjet printing onto the surface of a contact lens to build a single layer or multilayer structure the lens becomes a convenient, non-invasive drug delivery system that replaces the need to constantly apply eyedrops or the need for expensive, risky surgeries. This final product may then be worn for up to seven days, 30 days or more, constantly releasing drug over that period. One such drug that could be integrated into the coating is Latanoprost, a prostaglandin analog that is used in the treatment of glaucoma. The drug is first printed onto the dry lens surface in a single or multilayer 3D structure. After hydration, the printed wet lens is placed in packaging solution containing Latanoprost, and sterilized via steam sterilization.

One issue is the stability of Latanoprost throughout the manufacturing process, and the resulting product shelf life. The steam sterilization step catalyzes the degradation of Latanoprost—aqueous solutions of Latanoprost are susceptible to hydrolysis at the terminal ester, at temperatures greater than 4° C. The mechanism of degradation is in FIG. 1.

Latanoprost free acid, the main degradation product of Latanoprost, cannot easily pass into the cornea like Latanoprost, which diminishes the drug's IOP lowering effect. Therefore, it is of importance to reduce the exposure of Latanoprost to water as much as possible.

The general contact lens manufacturing process described above features multiple steps where Latanoprost is exposed to water. Namely, the hydration of dry contact lenses, and steam sterilization of Latanoprost-coated contact lenses pose risks to Latanoprost degradation. Furthermore, the contact lens is equilibrated in an aqueous packaging solution after sterilization. This adds another step where Latanoprost can degrade—if the drug diffuses from the coating into aqueous solution and undergoes hydrolysis, the resulting product is not therapeutically active, leaving less available drug. This poses a unique challenge in the manufacture of contact lenses containing Latanoprost, as there are few viable methods for sterilization of final product contact lenses aside from steam sterilization. Furthermore, the final product is commercially less viable if it needs to be stored at 5° C. or less. For example, Xalatan, the brand name for Latanoprost eye drops, must be store between 2-5° C. prior to opening. An alternative solution is desired in order to enable steam sterilization of drug-coated contact lenses, as well as enable greater tolerance in storage conditions after manufacturing. Achieving both would allow for the manufacture and stable storage of Latanoprost-coated contact lenses, which would introduce an alternative glaucoma treatment that is more convenient and easier to apply than eyedrops and less risky than regular surgeries for drug inserts.

In addition, it is desirable to control the drug release from the final product, in order to maintain a therapeutically effective Latanoprost release in the eye at the desired therapeutic level.

The previously covered issues in the production of Latanoprost-coated contact lenses can also be applied to other drugs, which are also heat-labile and subject to hydrolysis in aqueous solutions. One of these drugs is Atropine. Atropine may degrade in the following scheme as per FIG. 2.

Figure 2:
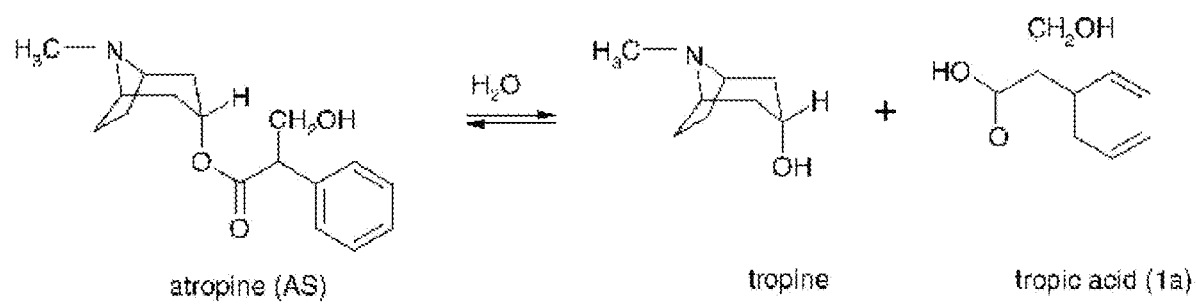
FIG. 2 generally depicts a proposed mechanism of Atropine Hydrolysis to Tropine and Tropic Acid.

Atropine is used to slow down the progression of myopia in children, but neither of the hydrolysis products in FIG. 2 are therapeutically active for the slowdown of myopia progression. Therefore, as with Latanoprost, it is of prime importance to reduce the exposure of Atropine to water as much as possible.

Figure 3:
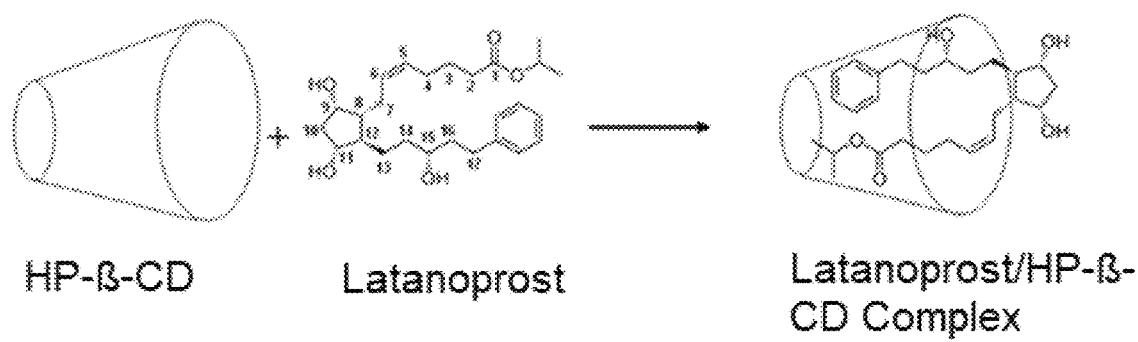
FIG. 3 generally depicts a proposed scheme for Latanoprost and 2-hydroxypropyl-β-cyclodextrin inclusion complex.

To allow for the steam sterilization of the final drug coated contact lenses, 2-hydroxypropyl-β-cyclodextrin (cyclodextrin) can be added to various manufacturing steps in the manufacturing process, as follows:
1. Addition of cyclodextrin into aqueous or oily phases of Latanoprost microemulsion
2. Addition of cyclodextrin into packaging solution
    Sawatdee et al. (Sawatdee, S. (2013, February 23). Development of a stable latanoprost solution for use as Eye Drops. Thai Science. https://www.thaiscience.info/journals/Article/CMJS/10886517.pdf) proposes that the hydrophobic portion of Latanoprost, including the ester, can nestle inside the ring, forming an occlusion complex that protects the molecule from hydrolysis. The molecule was also shown to be well-tolerated by humans, and as such is a promising potential solution to Latanoprost instability. One scheme for the complex formation is below in FIG. 3.

By adding 2-hydroxypropyl-β-cyclodextrin to microemulsion, packaging solution, or both, Latanoprost can complex with cyclodextrin, and thus be protected from hydrolysis. Optionally, cyclodextrin may also be added to the hydration solution to protect Latanoprost from hydrolysis. The proposed mechanisms for each addition are further explained below, thought applicant expressly does not limit the invention to a particular mechanism of action:

1. When cyclodextrin is added into the Latanoprost microemulsion, it provides a "safety net" component for Latanoprost. Cyclodextrin may be added into either the oil phase, or aqueous phase, or both phases.
   a. Cyclodextrin can be dissolved in Latanoprost directly, to form the complex in FIG. 3. Then, an oil may be added to the cyclodextrin-Latanoprost. An oil can be any substance that is not miscible with water without a surfactant. More preferable oils are fatty acids, and examples are included in Table 1.

TABLE 1

Preferable Oils and Concentrations for Microemulsion Preparation

| Surfactant | Concentration (% w/w) |
|---|---|
| Glyceryl monocaprylate | 2-10% |
| octanoic acid | 2-10% |
| stearic acid | 2-10% |

The listed oils are preferable, but not limited to only the oils in Table 1.

Figure 4:
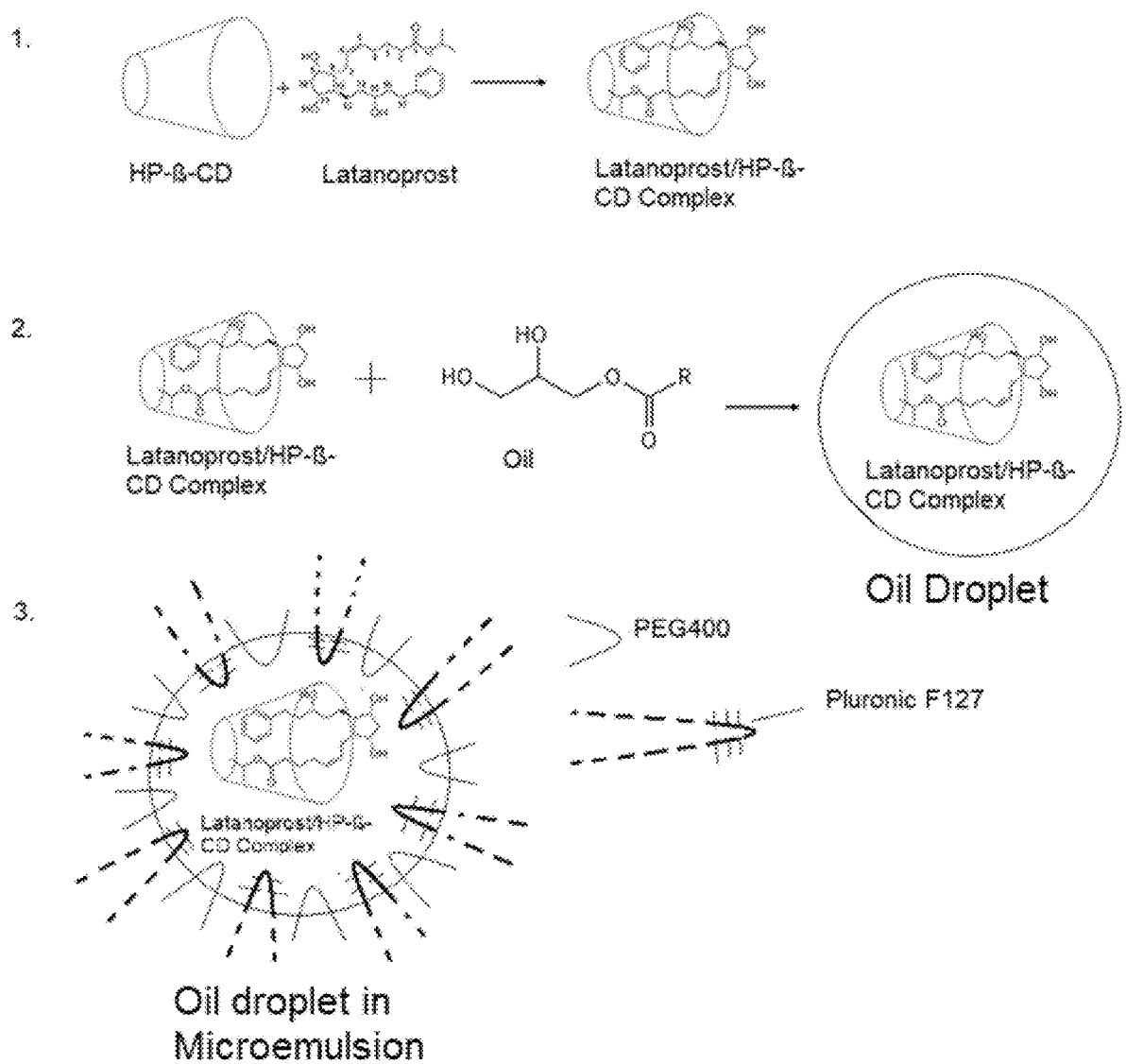
FIG. 4 generally depicts a proposed scheme for the formation of Latanoprost-cyclodextrin oil-in-water microemulsion system.

The cyclodextrin, Latanoprost, and oil is mixed until a homogenous solution is formed, called the "oily phase". The cyclodextrin-Latanoprost complex will dissolve into the oil, encapsulating the drug inside the oil. By adding cyclodextrin to the oil, the solubility of Latanoprost in the oily phase is increased. This serves to prevent Latanoprost from diffusing out of the oily phase, and away from the final product. To the oily phase is then added an aqueous phase, which contains a surfactant. The two phases are mixed until a homogenous microemulsion is formed. This is shown in the scheme below in FIG. 4.

b. Cyclodextrin can also be added into the aqueous phase of the microemulsion. If Latanoprost from the cyclodextrin-Latanoprost complex diffuses out of the oil droplets, cyclodextrin in the aqueous phase can complex with the diffused Latanoprost, in order to prevent Latanoprost from hydrolysis caused by water in the aqueous phase. This Latanoprost may then diffuse back to the oily phase of the microemulsion.

The microemulsion is then incorporated into a coating, that is then inkjet-printed onto dry contact lenses.

2. Cyclodextrin can be optionally added into the hydration solution. During the hydration of the dry drug-coated contact lenses, Latanoprost can diffuse out of the lens, and into hydration solution. If cyclodextrin is present in hydration solution, it can complex with any diffused Latanoprost, which will prevent Latanoprost from degradation. Then, Latanoprost may diffuse back onto the contact lens, which will improve the product's potency.

3. Cyclodextrin can also be added to the packaging solution, to act in the same fashion as addition to hydration solution. During sterilization and equilibration step of contact lens manufacturing, Latanoprost can diffuse from the drug coating to the aqueous packaging solution, where it can be hydrolyzed and become less therapeutically effective. Storage temperatures above 5° C. could exacerbate this effect, by both shifting the equilibration constant towards packaging solution and increasing the speed of hydrolysis degradation. If cyclodextrin is added to the packaging solution, any Latanoprost that diffuses from the contact lens to the packaging solution will complex with the present cyclodextrin, and this will protect Latanoprost from degradation. Furthermore, the complexed Latanoprost may diffuse back onto the contact lens coating, increasing the lens' therapeutic effect.

Adding cyclodextrin into all three components (microemulsion, hydration solution, and packaging solution) would increase the therapeutic effect and greatly extend the shelf life of any contact lens drug product with Latanoprost.

Mechanism 1a, addition of cyclodextrin to the oily phase of the microemulsion, can also be used as a method to modulate the drug release. By adding cyclodextrin, the solubility of Latanoprost is increased in oil, which reduces the rate of diffusion from microemulsion in the lens to outside the lens. This can slow the release rate of drug to be closer to zero-order kinetics, which will increase the potency of the final product.

Figure 5:
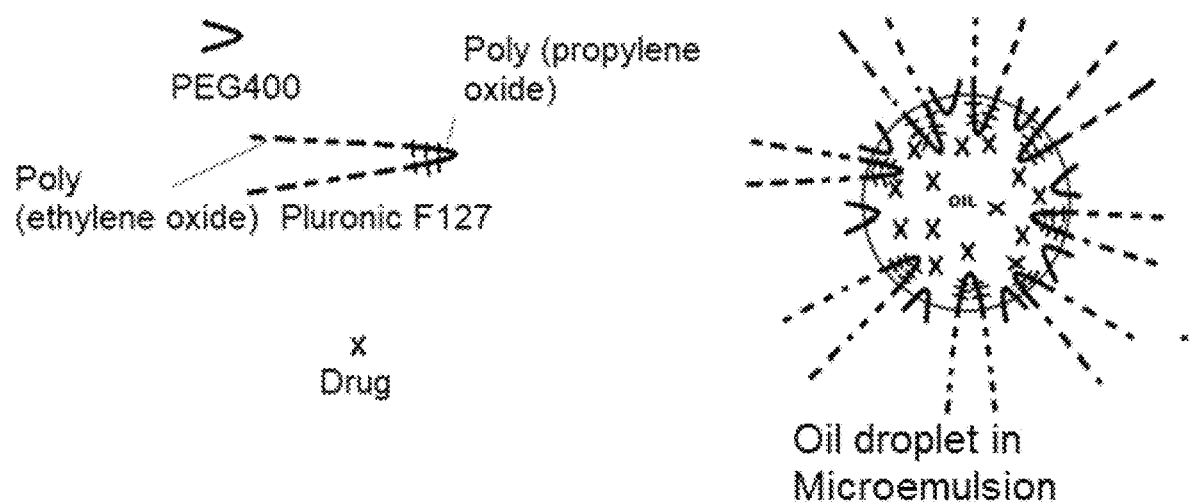
FIG. 5 generally depicts Latanoprost (Drug) dissolving in oil droplets in a microemulsion system.

The microemulsion (with or without cyclodextrin) can also be added to the packaging solution directly, in order to protect Latanoprost from degradation. By introducing oil droplets suspended in water, Latanoprost may theoretically dissolve in the oily phase of the microemulsion-packaging solution. If it is dissolved in the oil, there will be no water to hydrolyze Latanoprost, the main mechanism of degradation. This is shown in FIG. 5.

Different packaging solution formulations can be made, in order to test the effect of the different formulation on Latanoprost stability. One formulation contained 2-hydroxypropyl-β-cyclodextrin, which is a cyclic oligosaccharide with a hydrophobic "ring" interior.

Figure 6:
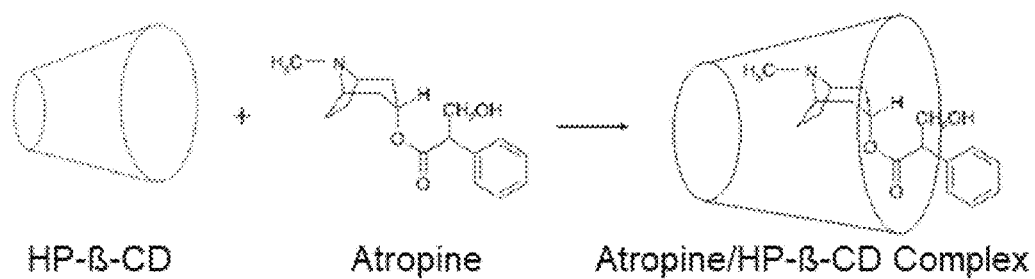
FIG. 6 generally depicts a proposed scheme for Atropine and 2-hydroxypropyl-β-cyclodextrin inclusion complex.

As with Latanoprost, 2-hydroxypropyl-β-cyclodextrin (cyclodextrin) can be used to prevent the degradation of Atropine. Cyclodextrin can be added to an Atropine drug final product as follows:

1. Addition of cyclodextrin into oily or aqueous phase of microemulsion
2. Addition of cyclodextrin into packaging solution Cyclodextrin functions in the same way for Atropine as it does for Latanoprost, as per FIG. 6.

Like for Latanoprost, cyclodextrin can act as a "safety net" for Atropine, if Atropine and cyclodextrin are dissolved in the aqueous phase of microemulsion or packaging solution. Cyclodextrin may also optionally be incorporated into hydration solution, to protect Atropine from hydrolysis. Cyclodextrin may also be incorporated into the oily phase, and increase the solubility of Atropine, as for Latanoprost. The cyclodextrin-microemulsion, when incorporated into the final lens product, will reduce the rate of diffusion out of the lens.

Examples: For Latanoprost, both approaches and a blank formulation with no additives were studied for at least two months at both 5° C.±3° C., and 25° C.±5° C. in order to document the change in assay value and the appearance of any new peaks that may be related to Latanoprost degradation. The following formulations of Latanoprost packaging solution were tested: a blank control solution with no additives, a solution with 10% microemulsion, and a solution with 2-hydroxypropyl-β-cyclodextrin. The formulations are below in Table 2, Table 3, Table 4, and Table 5:

TABLE 2

Blank Control (No Additive) Latanoprost Packaging Solution Formulation

| Material | % (w/w) |
|---|---|
| Sodium Chloride | 0.1-0.9 |
| Potassium Chloride | 0.01-0.09 |

TABLE 2-continued

Blank Control (No Additive) Latanoprost Packaging Solution Formulation

| Material | % (w/w) |
|---|---|
| Potassium Phosphate Monobasic | 0.01-0.09 |
| Disodium Phosphate | 0.1-0.9 |
| Latanoprost | 0.001-0.008 |
| Purified water or equivalent | 99 |
| Total | 100% |

TABLE 3

Microemulsion Formulation

| Microemulsion Formulation | % (w/w) |
|---|---|
| Pluronic F127 | 2-15% |
| Water | 2-15% |
| PEG 400 | 50-75% |
| Glyceryl Monocaprylate | 2-10% |
| Total | 100% |

TABLE 4

10% Microemulsion Packaging Solution Formulation

| Material | % (w/w) |
|---|---|
| Latanoprost Packaging Solution (Table 1) | 90 |
| Microemulsion (stabilizer) (Table 2) | 10 |

TABLE 5

2-Hydroxypropyl-β-Cyclodextrin Latanoprost Packaging Solution Formulation

| Material | % (w/w) |
|---|---|
| Sodium Chloride | 0.1-0.9 |
| Potassium Chloride | 0.01-0.09 |
| Potassium Phosphate Monobasic | 0.01-0.09 |
| Disodium Phosphate | 0.1-0.9 |
| Latanoprost | 0.001-0.008 |
| 2-Hydroxypropyl-β-Cyclodextrin (stabilizer) | 1-10 |
| Purified water or equivalent | 99 |
| Total | 100% |

100 g of Cyclodextrin formulation was prepared by measuring all non-water reagents according to the % (w/w) in Table 4 on an analytical balance, and then mixing with water for 1 hour via magnetic stirring. 100 g of blank control formulation was prepared with the % (w/w) given in Table 1 in the same fashion, by weighing all non-water reagents and mixing into water. Then, 45 g of the blank control formulation was mixed with 5 g of microemulsion (Table 2), to produce 55 g of blank control formulation and 50 g of microemulsion formulation (Table 3). Then, 2 mL of each solution was dispensed into 20 10-mL glass vials each, which were capped, crimped, and steam sterilized via autoclave. A portion of each solution was kept in 20-mL scintillation vials, and left unsterilized. Cyclodextrin formulation was prepared and sterilized, and blank control formulation and microemulsion formulation was prepared and sterilized. Both sterilized and unsterilized solution were tested at time zero and at regular intervals up to 3 months. All sterilized vials were kept in their crimped state until testing when they were opened.

At each testing interval, one previously-opened vial and two newly-opened vial were tested for all conditions, where applicable. The stability timepoints are shown below in Table 6:

TABLE 6

Stability Timepoint for Latanoprost Packaging Solution Formulation Assays
Time (Days)

| |
|---|
| 0 |
| 7 |
| 14 |
| 28 |
| 42 |
| 60 |
| 68* |
| 91* |

*Only 2-hydroxypropyl-β-cyclodextrin packaging solution was tested at Day 68 and 91.

The impurities 15-Keto-Latanoprost and Latanoprost free acid were purchased, and injected on the HPLC, to locate each impurities' retention time and relative retention time to Latanoprost. The HPLC method for assay and impurities is shown below in Table 7:

TABLE 7

HPLC Method used for Assay and Impurities of Latanoprost. Chromatographic Conditions:

| | |
|---|---|
| Mobile Phase: | 30:70 Water:ACN + 0.1% Formic Acid* |
| Injection Vol: | 100 μL |
| Flow Rate | 1 mL/min |
| Flow Time | 10 min |
| Col. Temp | 30° C. |
| Wavelength: | 210 nm |
| Column: | Phenomenex C18 Phenosphere-NEXT 5 μm 125 A, 250 × 4.6 mm P/N: 00G-4308-E0 |
| Machine: | HPLC2 (normal flow cell) |

*Analyses performed before Jun. 8, 2022 did not use 0.1% Formic Acid in the mobile phase. The results for control formulation of Latanoprost packaging solution, containing no additive, is below in Table 8.

TABLE 8

Blank Control Packaging Solution Stability over 2 Months

| Blank Control Formulation | Time (Days) | | | | | |
|---|---|---|---|---|---|---|
| Name | 0 | 7 | 14 | 28 | 42 | 61 |
| Unsterilized-5 C. (μg/mL) | 47.35 | 47.96 | 48.35 | 46.8 | 46.6 | 47.07 |

TABLE 8-continued

Blank Control Packaging Solution Stability over 2 Months

| Blank Control Formulation Name | Time (Days) | | | | | |
|---|---|---|---|---|---|---|
| | 0 | 7 | 14 | 28 | 42 | 61 |
| % Drop From Previous | — | 1.29% | 0.81% | −3.21% | −0.43% | 1.01% |
| % Drop Total Sterilized-5 C. (µg/mL) | 43.60 | 42.22 | 2.11% 42.16 | −1.16% 41.26 | −1.58% 42.23 | −0.59% 42.88 |
| % Drop From Previous | −7.93% | −3.16% | −0.13% | −2.13% | 2.36% | 1.53% |
| % Drop Total Unsterilized-25 C. (µg/mL) | 47.35 | 47.68 | −3.29% 47.39 | −5.36% 46.57 | −3.12% 47.15 | −1.64% 47.71 |
| % Drop From Previous | | 0.70% | −0.61% | −1.73% | 1.25% | 1.19% |
| % Drop Total Sterilized-25 C. (µg/mL) | 43.60 | 41.97 | 0.08% 39.97 | −1.65% 39.23 | −0.42% 37.56 | 0.76% 33.94 |
| % Drop From Previous | −7.93% | −3.73% | −4.77% | −1.84% | −4.27% | −9.63% |
| % Drop Total | | | −8.32% | −10.01% | −13.85% | −22.15% |

The assay data for sterilized solutions at each temperature were converted to percentages of the unsterilized assay, and the converted data is in Table 9.

TABLE 9

Sterilized Assay Values as Percentage of Unsterilized Assay Value

| No Excipient | Un-sterilized | 0 | 7 | 14 | 28 | 42 | 61 |
|---|---|---|---|---|---|---|---|
| 5° C. (µg/mL) | 47.35 | 43.595 | 42.216 | 42.16 | 41.26 | 42.23 | 42.88 |
| % | | 92% | 89% | 89% | 87% | 89% | 91% |
| 25° C. (µg/mL) | 47.35 | 43.595 | 41.97 | 39.966 | 39.23 | 37.56 | 33.94 |
| % | | 92% | 89% | 84% | 83% | 79% | 72% |

There is a 7.93% drop in assay value from unsterilized to sterilized at time 0, which indicates that this amount of Latanoprost degrades during the autoclave process. The unsterilized samples' assay values at both temperatures remain constant, which indicates that Latanoprost does not degrade if it is not autoclaved. Furthermore, the sterilized samples' assay value at 5° C. remain constant within analytical variance. This indicates that Latanoprost does not degrade at 5° C., past the initial autoclave degradation. However, Latanoprost shows a steady degradation trend at 25° C. Therefore, it can be concluded that Latanoprost in aqueous solution, without any additive, is not stable at 25° C.

The results for stability of 10% microemulsion packaging solution formulation is below in Table 10.

TABLE 10

10% Microemulsion Packaging Solution Stability over 2 Months

| 90:10 Water:ME Formulation Name | Time (Days) | | | | | |
|---|---|---|---|---|---|---|
| | 0 | 7 | 14 | 28 | 42 | 61 |
| Unsterilized-5 C. (µg/mL) | 46.33 | 46.54 | 44.58 | 44.88 | 45.61 | 46.75 |
| % Drop From Previous | — | 0.45% | −4.21% | 0.67% | 1.63% | 2.50% |
| % Drop Total | | | −3.78% | −3.13% | −1.55% | 0.91% |
| Sterilized-5 C. (µg/mL) | 40.08 | 43.76 | 42.38 | 42.41 | 40.95 | 41.61 |
| % Drop From Previous | −13.50% | 9.20% | −3.15% | 0.07% | −3.44% | 1.61% |
| % Drop Total | | | 5.75% | 5.83% | 2.18% | 3.83% |
| Unsterilized-25 C. (µg/mL) | 46.33 | 46.32 | 45.10 | 44.02 | 45.07 | 46.88 |
| %Drop From Previous | — | −0.02% | −2.63% | −2.39% | 2.39% | 4.02% |
| % Drop Total | | | −2.65% | −4.99% | −2.72% | 1.19% |
| Sterilized-25 C. (µg/mL) | 40.08 | 44.24 | 42.90 | 41.35 | 41.45 | 40.96 |
| % Drop From Previous | −13.50% | 10.39% | −3.04% | −3.60% | 0.25% | −1.19% |
| % Drop Total | | | 7.04% | 3.18% | 3.44% | 2.21% |

The assay data for sterilized solutions at each temperature were converted to percentages of the unsterilized assay, and the converted data is in Table 11.

TABLE 11

Sterilized Assay Values as Percentage of Unsterilized Assay Value

| 10% Microemulsion | Unsterilized | 0 | 7 | 14 | 28 | 42 | 61 |
|---|---|---|---|---|---|---|---|
| 5° C. (µg/mL) | 46.33 | 40.075 | 43.76 | 42.38 | 42.41 | 40.95 | 41.61 |
| % | | 86% | 94% | 91% | 92% | 88% | 90% |
| 25° C. (µg/mL) | 46.33 | 40.075 | 44.24 | 42.895 | 41.35 | 41.45333 | 40.96 |
| % | | 86% | 95% | 93% | 89% | 89% | 88% |

Like the blank control formulation, the 10% microemulsion formulation shows a large drop in Latanoprost assay during autoclave cycle. There is a 13.50% drop in assay value from unsterilized to sterilized concentration at Time 0. The unsterilized samples in both conditions are stable through 2 months. Similarly, after the initial drop, the sterilized samples in both conditions are stable through 2 months. There is no drop in assay value measured two months after sterilization in 25° C. test group. Therefore, it can be concluded that the addition of microemulsion stabilizes Latanoprost in aqueous solution at 25° C., and that this addition is necessary for stabilization.

The results for stability of 2-Hydroxypropyl-β-Cyclodextrin packaging solution formulation is below in Table 12.

The unsterilized sample stored at 25° C. showed rapid degradation starting from 1-month onwards (28 days). However, because the sterilized samples do not show the same degradation trend, the unsterilized sample was removed from testing and the observed results will be regarded as an outlier. The degradation is most likely due to contamination of the unsterilized sample.

The assay data for sterilized solutions at each temperature, at each month, were converted to percentages of the unsterilized assay, and the converted data is in Table 13.

The 2-Hydroxypropyl-β-Cyclodextrin formulations show a large drop during autoclaving, similar to the other two formulations. The 5° C. sterilized samples show stability through 3 months. The 25° C. sample shows a 6.14% assay, which indicates that with further optimization, 2-hydroxypropyl-β-cyclodextrin could be a viable additive to the packaging formulation to stabilize Latanoprost at 25° C.

TABLE 12

2-Hydroxypropyl-ß-Cyclodextrin Packaging Solution Stability over 3 Months

| 2-HP-ß-CD Name | Time (Days) | | | | | | | |
|---|---|---|---|---|---|---|---|---|
| | 0 | 7 | 14 | 28 | 42 | 56 | 68 | 91 |
| Unsterilized-5 C. (µg/mL) | 123.44 | 125.1 | 124.84 | 123.41 | 123.04 | 121.47 | 127.22 | 123.67 |
| % Drop From Previous | — | 1.34% | -0.21% | -1.15% | -0.30% | -1.28% | 4.73% | -2.79% |
| % Drop Total | | | 1.13% | -0.02% | -0.32% | -1.60% | 3.06% | 0.19% |
| Sterilized-5 C. (µg/mL) | 116.55 | 118.30 | 117.90 | 115.92 | 116.09 | 116.26 | 116.36 | 113.90 |
| % Drop From Previous | -5.58% | 1.50% | -0.34% | -1.68% | 0.15% | 0.15% | 0.09% | -2.12% |
| % Drop Total | | | 1.16% | -0.54% | -0.39% | -0.25% | -0.16% | -2.27% |
| Unsterilized-25 C. (µg/mL) | 123.44 | 117.03 | 123.48 | 108.32 | 60.05 | 21.99 | | |
| % Drop From Previous | — | -5.19% | 5.51% | -12.28% | -44.56% | -63.38% | | |
| % Drop Total | | | 0.03% | -12.25% | -51.35% | -82.19% | | |
| Sterilized-25 C. (µg/mL) | 116.55 | 116.43 | 115.36 | 112.31 | 112.05 | 107.46 | 113.10 | 108.97 |
| % Drop From Previous | -5.58% | -0.10% | -0.92% | -2.64% | -0.23% | -4.10% | 5.25% | -3.65% |
| % Drop Total | | | -1.02% | -3.64% | -3.86% | -7.80% | -2.96% | -6.50% |

TABLE 13

Sterilized Assay Values as Percentage of Unsterilized Assay Value

| 2-Hydroxypropyl-β-Cyclodextrin | Unsterilized | 0 | 28 | 56 | 91 |
|---|---|---|---|---|---|
| 5° C. (µg/mL) | 123.44 | 116.55 | 115.92 | 116.26 | 113.90 |
| % | | 94.42% | 93.91% | 94.18% | 92.27% |
| 25° C. (µg/mL) | 123.44 | 116.55 | 112.31 | 107.46 | 108.97 |
| % | | 94.42% | 90.98% | 87.05% | 88.28% |

Figure 7:
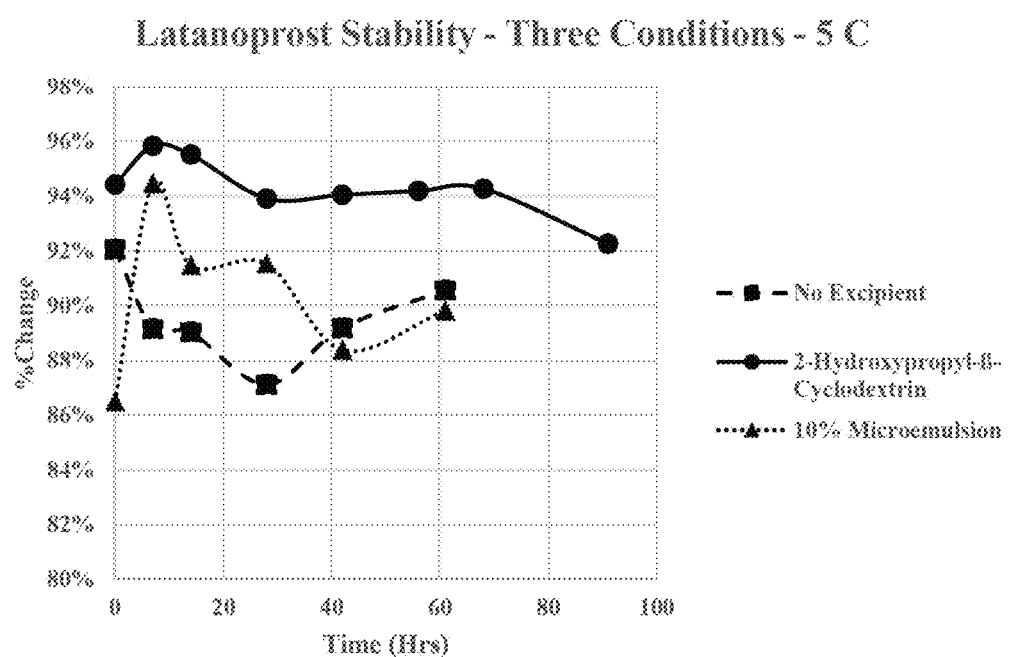
FIG. 7 generally depicts Latanoprost Packaging Solution Stability at 5° C.
Figure 8:
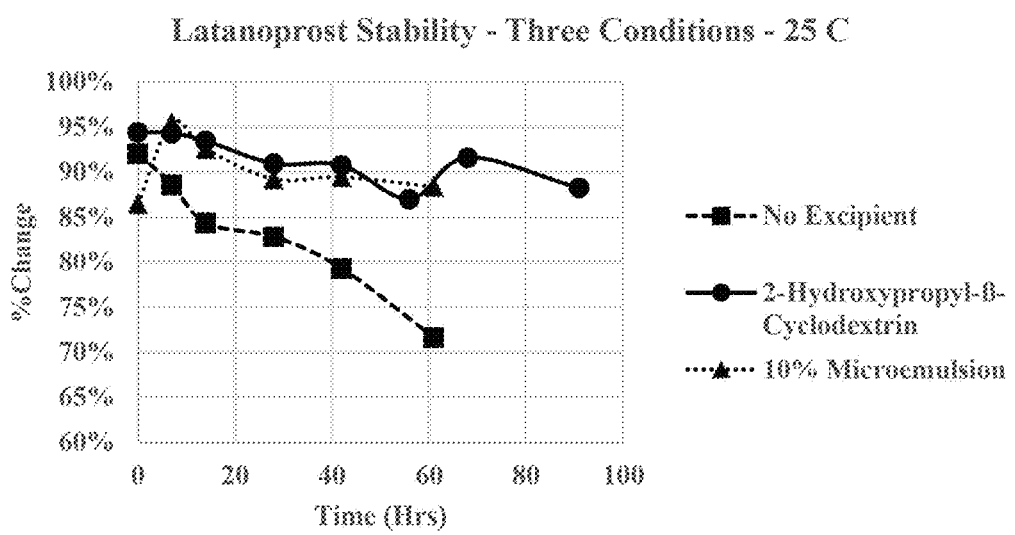
FIG. 8 generally depicts Latanoprost Packaging Solution Stability at 25° C.

The overall stability graphs for 5° C. and 25° C. are in FIG. 7 and FIG. 8, respectively.

In the 5° C. condition, none of the formulations, including the blank control formulation, showed degradation over at least 2 months. In the 25° C. condition, only the blank control formulation showed degradation over 2 months. This suggests that both 2-hydroxypropyl-β-cyclodextrin and 10% microemulsion are effective and necessary for the stabilization of Latanoprost in aqueous solution.

The chromatograms of the final assay timepoints were evaluated for the presence of 15-keto Latanoprost, an oxidation impurity, and Latanoprost Free Acid, the hydrolysis impurity, see Table 14.

TABLE 14

Impurities Present in Latanoprost Stability Samples at 25° C.

| | Timepoint (Days) | Latanoprost Free Acid (μg/mL) | 15-Keto-Latanoprost (μg/mL) |
|---|---|---|---|
| Blank Control Formulation | Time Zero | — | — |
| | 7 | — | — |
| | 14 | — | — |
| | 28 | 1.03 | — |
| | 42 | 1.03 | — |
| | 61 | 2.08 | — |
| 10% Microemulsion Formulation | Time Zero | — | — |
| | 7 | — | — |
| | 14 | — | — |
| | 28 | — | — |
| | 42 | — | — |
| | 61 | — | — |
| 2-Hydroxypropyl-β-Cyclodextrin Formulation | Time Zero | — | — |
| | 7 | — | — |
| | 14 | — | — |
| | 28 | 2.62 | — |
| | 42 | 3.72 | — |
| | 56 | 3.78 | — |
| | 68 | 4.15 | — |
| | 91 | 4.70 | — |

In contrast to the other two formulations, the microemulsion chromatograms do not show any impurity peaks that cannot be accounted for from the blank microemulsion chromatogram, which suggests that the addition of microemulsion greatly decreases the rate of hydrolysis.

15-Keto-Latanoprost was not detected in any sample, which suggests that oxidation of Latanoprost is not a major contributor to Latanoprost instability in steam-sterilized aqueous packaging solutions.

In blank control and 2-Hydroxypropyl-β-Cyclodextrin Formulation, Latanoprost free acid was observed to form.

Between 2-hydroxypropyl-β-cyclodextrin and microemulsion, the microemulsion appears to be more effective at stabilizing Latanoprost at 25° C. The main degradation product observed in the blank control formulation, Latanoprost free acid, is not present in any sample of microemulsion formulation from time zero to two months. Furthermore, the assay value of the sterilized microemulsion samples did not show a stability-based degradation trend. The assay value at 2 months shows a 2.21% increase from time zero, which suggests that there is no degradation of Latanoprost in the sample. In contrast, 2-hydroxypropyl-β-cyclodextrin formulations show a change of −7.86% from time zero in two months, and −6.50% from time zero in three months. In addition, the impurity Latanoprost free acid was observed in the 2-hydroxypropyl-β-cyclodextrin samples from one month onwards. The concentration of the impurity peak also increased with time, which suggests the process of hydrolysis continues over time (Table 13). This suggests that 2-hydroxypropyl-β-cyclodextrin as an additive slows the degradation of Latanoprost, but does not stop hydrolysis altogether. Both additives are an improvement over the blank control formulation, which shows a −22.15% decrease in assay value over two months, with a corresponding increase in Latanoprost free acid concentration (Table 13). Because the blank control formulation shows a stability-based degradation trend, it can be concluded that the addition of microemulsion or 2-hydroxypropyl-β-cyclodextrin can stabilize Latanoprost in an aqueous solution at temperatures exceeding 5° C.

Example 2: Latanoprost-Coated Contact Lenses Packaged in Stabilized Latanoprost Packaging Solution Drug coated contact lenses were prepared, and packaged and sterilized in the cyclodextrin-packaging solution, as detailed in Example 1. The drug coated contact lenses were prepared with the following formulations:

Formulations

1. Microemulsion Formulations (for Ink/Coating)

1.1. LAT-ME Preparation 1.1.1. Latanoprost micro emulsion was prepared in two parts, the aqueous phase and oily phase. The aqueous phase was prepared by mixing Pluronic F127, Water, and PEG 400. This mixture was then sonicated for 10 min and allowed to mix for 12 hours until clear. Oily phase was prepared by mixing Latanoprost and Capmul MCM C-8-EP and sonicating for 10 minutes. The oily phase was allowed to mix for 12-24 hours. The aqueous phase was added to the oily phase and allowed to mix for 12-24 hours. The formulation is below in Table 15:

TABLE 15

Latanoprost-Microemulsion Formulation

| Material | Percentage |
|---|---|
| Aqueous Phase | |
| Pluronic F127 | 1-25 |
| Water | 1-25 |
| PEG 400 | 75-99 |
| Oily Phase | — |
| Latanoprost | 1-25 |
| Capmul MCM C-8-E | 1-25 |

1.2. Cyclodextrin Latanoprost-ME Preparation

A cyclodextrin Latanoprost-microemulsion formulation can be prepared. This formulation is prepared by first mixing Latanoprost and cyclodextrin, then mixing with Capmul MCM C-8-EP for about 12-24 hours, to make oily phase. Pluronic F127, water, and PEG 400 are mixed concurrently, for about 12-24 hours, to make aqueous phase. Once both solutions are fully formed (no undissolved particulates remaining), the aqueous phase is added dropwise to the oily phase, and the two solutions are mixed for 12-24 hours, or until a single solution is formed. The formulation is as per Table 16:

TABLE 16

Cyclodextrin Latanoprost-Microemulsion Formulation

| Latanoprost Microemulsion Formulation | % (w/w) |
|---|---|
| Pluronic F127 | 2-15% |
| Water | 2-15% |
| PEG 400 | 50-75% |
| Latanoprost | 5-20% |
| Cyclodextrin | 1-5% |
| Capmul MCM C-8-EP | 2-10% |
| Total | 100% |

2. Other Ink Additives
2.1. Tween-HA Preparation
   2.1.1. In addition, Hylan A (Hyaluronic Acid, HA) has been shown to both increase Latanoprost solubility in solution as well as increase the ability of Latanoprost to cross corneal tissues, thus increasing bioavailability of the drug. Hyaluronic Acid is a polysaccharide molecule naturally found in the body. It retains water within its structure, which makes HA useful as a lubricating agent, to retain moisture on the eye. It also reduces protein deposits on the eye. HA can be used in the contact lens drug delivery system as a comforting agent, in order to wear the lens comfortably for a week, for the above reasons. Tween-HA, a mixture of Tween-20 and HA is included in the ink to incorporate HA into the lens. The formulation for Tween-HA is shown below in Table 17.

TABLE 17

Tween-HA Formulation

| Material | Percentage |
|---|---|
| Tween-20 | 10-40 |
| Sodium Hyaluronate | 60-80 |

2.1. Masterbatch Preparation
   2.1.1. The masterbatch forms the basis of the UV coating, and includes oligomer as well as various monomers that can undergo radical polymerization. The formulation is in Table 18.

TABLE 18

Masterbatch Formulation

| Material | Percentage |
|---|---|
| SR-344 (PEGDA400) | 1-10 |
| MPO Oligomer | 10-25 |
| NVP | 5-20 |
| GMMA | 5-20 |
| HEMA | 30-70 |

3. Ink Formulations
3.1. LAT-ME-HA Coating Solution Preparation
   3.1.1. Latanoprost-microemulsion-hyaluronic acid coating solution is prepared by mixing LAT-microemulsion with Masterbatch. This mixture is then added to the auto-triturator along with Tween-HA and allowed to triturate. The coating is then sonicated, then homogenized. 1-Ethoxy-2-propanol is used as a diluent for the coating and is added until the desired printing viscosity for the coating solution is obtained. The formulation is in Table 19:

TABLE 19

LAT-ME-HA Coating Solution Preparation for Coating Contact Lenses

| Material | Percentage |
|---|---|
| LAT-Microemulsion[1] | 1-20 |
| Tween-HA | 1-20 |
| Masterbatch | 50-99 |

1. Cyclodextrin Latanoprost-Microemulsion may also be used in preparation of LAT-ME-HA Coating
   After LAT-ME-HA Coating is prepared, polymerization initiators are dissolved in solution, which when activated, produce free radicals during the inkjet printing process. Table 20 shows the formulation for LAT-ME-HA-UV coating:

TABLE 20

LAT-ME-HA-UV Coating Solution Preparation for Coating Contact Lenses

| Material | Percentage |
|---|---|
| LAT-ME-HA Coating | 80-95 |
| Omnirad 184 | 1-10 |
| Omnirad 819 | 1-10 |

4. Packaging Solution Formulations
4.1. LAT PS Stabilized with Cyclodextrin
   4.1.1. Latanoprost packaging solution that is stabilized with 2-hydroxypropyl-beta-cyclodextrin is prepared based on desired concentration of Latanoprost. The buffering salts, 2-hydroxypropyl-beta-cyclodextrin, and water are mixed until completely dissolved. Then latanoprost is allowed to mix for about 4 hours with the solution until it has dissolved. Then sodium hyaluronate is added and mixed until completely dissolved. The solution is then filtered. The pH of the packaging solution is measured and if necessary, adjusted to a desired range of 7.0-7.4. The formulation is in Table 21:

TABLE 21

Latanoprost PS Formulation

| Material | Percentage |
|---|---|
| Sodium Chloride | 0.1-1 |
| Potassium Chloride | 0.01-0.05 |
| Potassium Phosphate Monobasic | 0.01-0.05 |
| Disodium Phosphate | 0.05-0.5 |
| Sodium Hyaluronate | 0.05-0.3 |
| Latanoprost | 0.01-1 |
| 2-Hydroxypropyl-β-Cyclodextrin | 0.1-1 |
| Water | 90-99 |

LAT-ME-HA-UV coating solution was prepared, and a single layer of coating was printed onto dry contact lens via an inkjet printing setup, using a Piezzo printerhead to dispense coating solution. The lenses were cured under UV light, to polymerize the coating, and thus form the drug coated contact lens. These drug coated contact lenses were hydrated in a 0.05% $NaHCO_3$ solution, and packaged in Latanoprost packaging solution. The lenses and packaging solution were sterilized, to form the final product drug-coated contact lenses.

Figure 9:
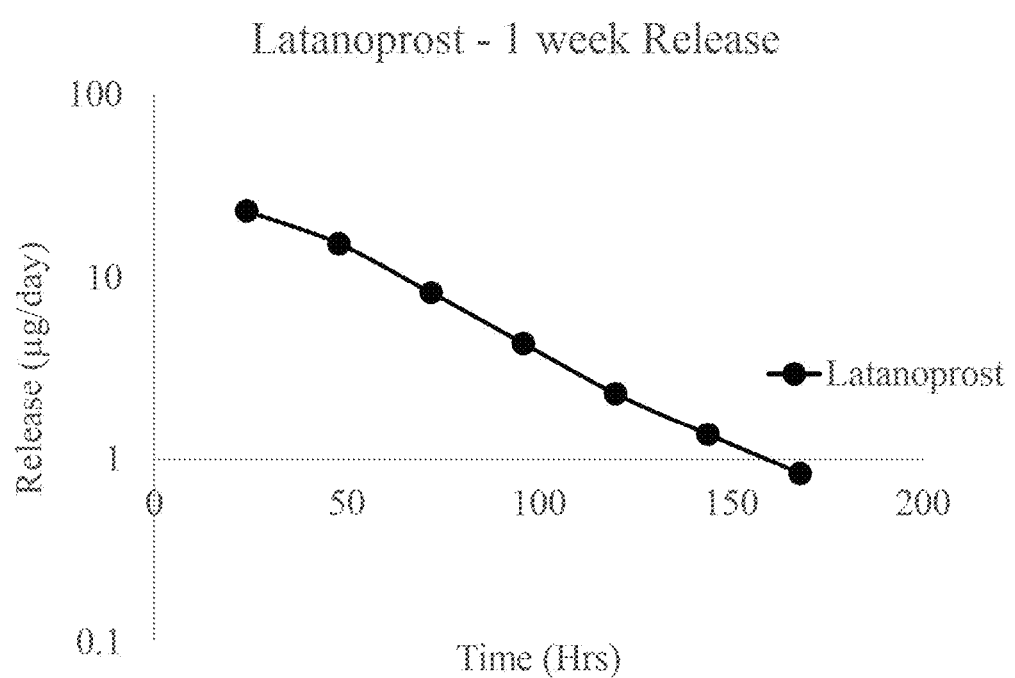
FIG. 9 generally depicts daily release of Latanoprost printed on lenses over a one-week period.
Figure 10:
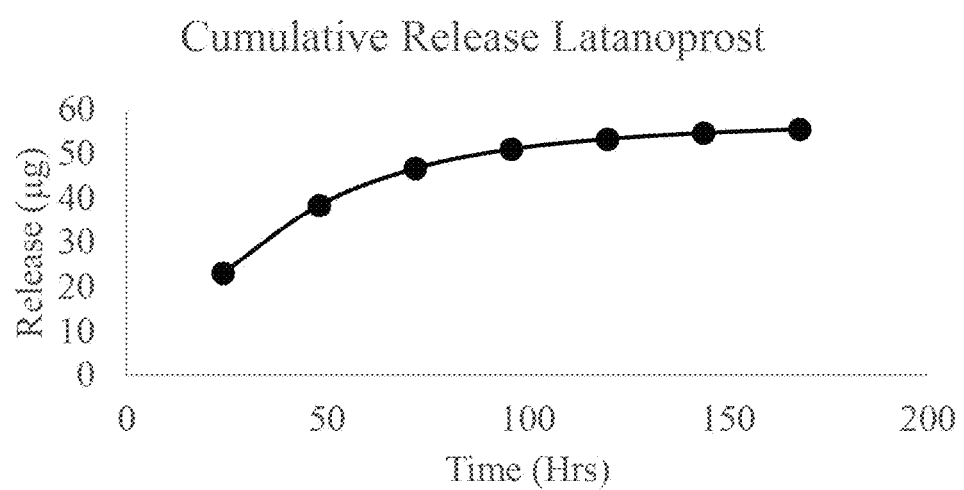
FIG. 10 generally depicts the cumulative release of Latanoprost in lens over a one-week period.

Performance of the lenses that have been manufactured in accordance with the present invention, particularly as set forth in the Examples, have been characterized with a 1-week release graph of a batch of combination drug contact lenses. FIG. 9 and FIG. 10 show the daily release and cumulative release of Latanoprost from the contact lens.

In an in-vitro setting, Latanoprost was shown to release on each day for a seven-day period from a drug-coated contact lens, sterilized in a Latanoprost packaging solution containing cyclodextrin.

All publications, including patent documents and scientific articles, referred to in this application and the bibliography and attachments are incorporated by reference in their entirety for all purposes to the same extent as if each individual publication were individually incorporated by reference.

All headings are for the convenience of the reader and should not be used to limit the meaning of the text that follows the heading, unless so specified.

What is claimed is:

1. A packaged medical device, comprising:
   a) at least one drug delivery contact lens, comprising:
      i) at least one coating provided on at least one surface of said drug delivery contact lens;
         where said at least one coating comprises at least one emulsion;
      ii) at least one hydrophobic drug;
         wherein said at least one hydrophobic drug comprises at least one prostaglandin, at least one prostaglandin derivative, or a combination thereof;
      wherein said at least one coating comprises said at least one hydrophobic drug;
         wherein said at least one hydrophobic drug is subject to degradation by hydrolysis;
         further wherein said at least one hydrophobic drug is incorporated into at least one emulsion;
   b) at least one packaging solution, comprising:
      1) said at least one hydrophobic drug;
      2) at least one emulsion;
   c) at least one packaging, comprising:
      1) said at least one drug delivery contact lens; and
      2) said at least one packaging solution;
      d) further wherein said at least one hydrophobic drug is stabilized against hydrolysis in said at least one drug delivery contact lens, in said at least one packaging solution, or a combination thereof, under conditions of steam sterilization, heat, or a combination thereof, at temperatures of up to 100° C. or above.

2. The packaged medical device of claim 1;
   wherein said at least one coating is made in whole or in part by additive printing.

3. The packaged medical device of claim 2;
   wherein said additive printing comprises ink jet printing.

4. The packaged medical device of claim 2;
   wherein said additive printing comprises digital printing, 3D printing, digital 3D printing, pad printing, or a combination thereof.

5. The packaged medical device of claim 1;
   wherein said at least one hydrophobic drug comprises latanoprost, or bimatoprost, or combinations thereof.

6. The packaged medical device of claim 1;
   wherein said at least one hydrophobic drug comprises latanoprost.

7. The packaged medical device of claim 1;
   wherein said at least one hydrophobic drug is stabilized by said at least one emulsion, against hydrolysis in said drug delivery contact lens, or in said packaged medical device, or said at least one coating, or said at least one packaging solution, or combinations thereof.

8. The packaged medical device of claim 1;
   wherein said at least one emulsion comprises at least one microemulsion.

9. The packaged medical device of claim 1;
   wherein said at least one emulsion comprises at least one oil-in water emulsion, at least one oil-in water microemulsion, or a combination thereof.

10. The packaged medical device of claim 1;
    wherein said drug delivery contact lens comprises:
    a) a soft contact lens;
    b) a multifocal contact lens; or
    c) a combination thereof.

11. The packaged medical device of claim 1;
    wherein release of said at least one hydrophobic drug from said at least one drug delivery contact lens is modulated by the physical properties of said at least one drug delivery lens, the chemical properties of said at least one drug delivery lens, or a combination thereof.

12. The packaged medical device of claim 11;
    wherein said physical properties of said drug delivery lens comprise structures or conditions provided by said additive printing, or a combination thereof.

13. The packaged medical device of claim 1;
    wherein said at least one coating comprises one or more layers.

14. The packaged medical device of claim 1;
    wherein said at least one hydrophobic drug is provided in a pharmaceutically effective amount.

15. The packaged medical device of claim 1;
    wherein said at least one hydrophobic drug is heat labile.

16. The packaged medical device of claim 1;
    wherein said at least one hydrophobic drug in said at least one drug delivery contact lens, in said at least one packaging solution, or a combination thereof, is steam stabilized, heat stabilized, hydrolysis stabilized, or a combination thereof.

17. The packaged medical device of claim 1;
    wherein said at least one emulsion comprises oil droplets in a water medium to form at least one emulsion, at least one microemulsion, or a combination thereof.

18. The packaged medical device of claim 1;
    wherein said at least one packaging comprises at least one blister pack.

19. The packaged medical device of claim 1;
    wherein said at least one packaging comprises at least one vial.

20. The packaged medical device of claim 1;
    wherein said packaged medical device, said at least one drug delivery contact lens, said at least one packaging solution, or a combination thereof, comprise at least one additional drug.

21. The packaged medical device of claim 20;
    wherein said at least one additional drug is provided in a pharmaceutically effective amount.

22. The packaged medical device of claim 20;
    wherein said at least one additional drug comprises at least one hydrophilic drug.

23. The packaged medical device of claim 20;
wherein said at least one additional drug further comprises at least one hydrophobic drug.

24. The packaged medical device of claim 20;
wherein said at least one additional drug is selected from the group consisting of an antibiotic, an intraocular pressure reducing agent, a comfort enhancing agent, an anti-inflammatory agent, a penetration enhancer, a macular degeneration agent, a diabetic retinopathy agent, and combinations thereof.

25. The packaged medical device of claim 20;
wherein said at least one additional drug further comprises dorzolamide, timolol, or a combination thereof.

26. The packaged medical device of claim 20;
wherein said at least one additional drug is selected from the group consisting of timolol, alphagan, axopt, cosopt, lumigan, travatan, xalatan, combigan, timolol hemihydrate, betaxolol, levobunolol, metipranolol, apraclonidine, Brimonidine tartate, Brinzolamide, methazolamide, dorzolamide, acetazolamide, carbachol, travoprost, latanoprostene bunod, tafluprost, netarsudil, and combinations thereof.

27. The packaged medical device of claim 20;
wherein said at least one additional drug is selected from the group consisting of sodium hyaluronate, hyaluronic acid, cyclosporine, polyethylene glycol 400, hypromellose, polyvinyl alcohol, carboxymethylcellulose, dextran 70, hydroxypropyl methylcellulose, anhydrous liquid lanolin, mineral oil, white petroleum, mannitol, thiomersal, carbomer, cetrimide, glycerin, polysorbate80, povidone, and combinations thereof.

28. The packaged medical device of claim 20; wherein said at least one additional drug is selected from the group consisting of perdforte, lotemax, fluromethlone, nevanac, acular, xibrom, and combinations thereof.

29. The packaged medical device of claim 20;
wherein said at least one additional drug is selected from the group consisting of Flurbiprofen, Acetazolamide, ethylenediaminetetraacetic acid, palmitoyl carnitine, sodium caprate, sodium dodecylsulphate, sodium deoxycholate, poly oxyethylene-g-lauryl ether, 1-α-lysophosphatidylocholine, deoxycholate, taurodeoxycholate, glycocholate, benzalkonium chloride, and combinations thereof.

30. The packaged medical device of claim 20;
wherein said at least one additional drug comprises aflibercept.

31. The packaged medical device of claim 20;
wherein said at least one additional drug is selected from the group consisting of dexamethasone, at least one steroid, pilocarpine nitrate, tropicamide, methyl prednisolone, flurbiprofen, penicillin, ciprofloxacin, sulphacetaminde sodium, indomethacin, hydrocortisone, indomethacin, ciprofloxacin hydrochloride, insulin, indomethacin, ketorolac tromethamine, and combinations thereof.

32. The packaged medical device of claim 20;
wherein said at least one additional drug is selected from the group consisting of gentamicin, tobramycin, erythromycin, polytrim, cirproflizacin, viamox, xymar, and combinations thereof.

33. A drug delivery contact lens, comprising:
a) coating provided on at least one surface of said drug delivery contact lens;
where said at least one coating comprises at least one emulsion;
b) at least one hydrophobic drug;
wherein said at least one hydrophobic drug comprises at least one prostaglandin, at least one prostaglandin derivative, or a combination thereof;
wherein said at least one coating comprises said at least one hydrophobic drug;
wherein said at least one hydrophobic drug is subject to degradation by hydrolysis;
further wherein said at least one hydrophobic drug is incorporated into at least one emulsion,
further wherein said at least one hydrophobic drug is stabilized against hydrolysis in said drug delivery contact lens under conditions of steam sterilization, heat, or a combination thereof, at temperatures of up to 100° C., or above.

34. The drug delivery contact lens of claim 33;
wherein said at least one coating is made in whole or in part by additive printing.

35. The drug delivery contact lens of claim 34;
wherein said additive printing comprises ink jet printing.

36. The drug delivery contact lens of claim 34;
wherein said additive printing comprises digital printing, 3D printing, digital 3D printing, pad printing, or a combination thereof.

37. The packaged medical device of claim 33;
wherein said at least one hydrophobic drug comprises latanoprost, bimatoprost, or a combination thereof.

38. The packaged medical device of claim 33;
wherein said at least one hydrophobic drug comprises latanoprost.

39. The packaged medical device of claim 33; wherein said hydrophobic drug is stabilized by said at least one emulsion, against hydrolysis in said drug delivery contact lens, or in said packaged medical device, or said at least one coating, or said at least one packaging solution, or combinations thereof.

40. The drug delivery contact lens of claim 33;
wherein said at least one emulsion comprises at least one microemulsion.

41. The drug delivery contact lens of claim 33;
wherein said at least one emulsion comprises at least one oil-in water emulsion, at least one oil-in water microemulsion, or a combination thereof.

42. The drug delivery contact lens of claim 33;
wherein said drug delivery contact lens comprises:
a) a soft contact lens;
b) a multifocal contact lens; or
c) a combination thereof.

43. The drug delivery contact lens of claim 33;
wherein the release of said at least one hydrophobic drug from said drug delivery contact lens is modulated by the physical properties of said drug delivery lens, the chemical properties of said drug delivery lens, or a combination thereof.

44. The drug delivery contact lens of claim 43;
wherein said physical properties of said drug delivery lens comprise structures or conditions provided by said additive printing, or a combination thereof.

45. The drug delivery contact lens of claim 33;
wherein said at least one coating comprises one or more layers.

46. The drug delivery contact lens of claim 33;
wherein said at least one hydrophobic drug is provided in a pharmaceutically effective amount.

47. The drug delivery contat lens of claim 33;
wherein said at least one hydrophobic drug is heat labile.

48. The drug delivery contact lens of claim 33;
wherein said at least one emulsion comprises oil droplets in a water medium to form at least one emulsion, at least one microemulsion, or a combination thereof.

49. The drug delivery contact lens of claim 33;
wherein said drug delivery contact lens comprises at least one additional drug.

50. The drug delivery contact lens of claim 49;
wherein said at least one additional drug is provided in a pharmaceutically effective amount.

51. The drug delivery contact lens of claim 49;
wherein said at least one additional drug comprises at least one hydrophilic drug.

52. The drug delivery contact lens of claim 49;
wherein said at least one additional drug comprises at least one hydrophobic drug.

53. The drug delivery contact lens of claim 49;
wherein said at least one additional drug comprises an antibiotic, an intraocular pressure reducing agent, a comfort enhancing agent, an anti-inflammatory agent, a penetration enhancer, a macular degeneration agent, diabatic retinopathy agent, or a combination thereof.

54. A method of treating at least one disease, or disorder, or condition of an eye of a subject in need of treatment thereof, the method comprising;
   a) providing at least one packaged medical device of claim 1;
   b) providing a subject in need of treatment of at least one disease, or disorder, or condition of an eye of said subject, by said at least one drug in at least one drug delivery contact lens;
   c) operably engaging said at least one drug delivery contact lens on an eye of said subject;
   d) wherein said subject is treated for said at least one disease, or disorder, or condition of an eye of said subject, by said at least one drug in said at least one drug delivery contact lens.

55. The method of treating at least one disease, or disorder, or condition of an eye of a subject in need of treatment thereof of claim 54;
wherein said disease, disorder, or condition of the eye comprises
   a) glaucoma;
   b) myopia; or
   c) a combination thereof.

56. The method of treating at least one disease, or disorder, or condition of an eye of a subject in need of treatment thereof of claim 54;
wherein said at least one coating is made in whole or in part by additive printing.

57. The method of treating at least one disease, or disorder, or condition of an eye of a subject in need of treatment thereof of claim 56;
wherein said additive printing comprises ink jet printing.

58. The method of treating at least one disease, or disorder, or condition of an eye of a subject in need of treatment thereof of claim 56;
wherein said additive printing comprises digital printing, 3D printing, digital 3D printing, pad printing, or combinations thereof.

59. The method of treating at least one disease, or disorder, or condition of an eye of a subject in need of treatment thereof of claim 54;
wherein said at least one hydrophobic drug comprises latanoprost, bimatoprost, or combinations thereof.

60. The method of treating at least one disease, or disorder, or condition of an eye of a subject in need of treatment thereof of claim 54;
wherein said at least one hydrophobic drug comprises latanoprost.

61. The method of treating at least one disease, or disorder, or condition of an eye of a subject in need of treatment thereof of claim 54;
wherein said at least one hydrophobic drug is stabilized by said at least one emulsion, against hydrolysis in said drug delivery contact lens, or in said packaged medical device, or said at least one coating, or said at least one packaging solution, or combinations thereof.

62. The method of treating at least one disease, or disorder, or condition of an eye of a subject in need of treatment thereof of claim 54;
wherein said at least one emulsion comprises at least one microemulsion.

63. The method of treating at least one disease, or disorder, or condition of an eye of a subject in need of treatment thereof of claim 54;
wherein said at least one emulsion comprises at least one oil-in water emulsion, at least one oil-in water microemulsion, or a combination thereof.

64. The method of treating at least one disease, or disorder, or condition of an eye of a subject in need of treatment thereof of claim 54;
wherein said drug delivery contact lens comprises:
   a) a soft contact lens;
   b) a multifocal contact lens; or
   c) a combination thereof.

65. The method of treating at least one disease, or disorder, or condition of an eye of a subject in need of treatment thereof of claim 54;
wherein release of said at least one hydrophobic drug from said drug delivery contact lens is modulated by the physical properties of said drug delivery contact lens, the chemical properties of said drug contact delivery lens, or a combination thereof.

66. The method of treating at least one disease, or disorder, or condition of an eye of a subject in need of treatment thereof of claim 65;
wherein said physical properties of said drug delivery lens comprise structures or conditions provided by said additive printing, or a combination thereof.

67. The method of treating at least one disease, or disorder, or condition of an eye of a subject in need of treatment thereof of claim 54;
wherein said at least one coating comprises one or more layers.

68. The method of treating at least one disease, or disorder, or condition of an eye of a subject in need of treatment thereof of claim 54;
wherein said at least one hydrophobic drug is provided in a pharmaceutically effective amount.

69. The method of treating at least one disease, or disorder, or condition of an eye of a subject in need of treatment thereof of claim 54;
wherein said at least one hydrophobic drug is heat labile.

70. The method of treating at least one disease, or disorder, or condition of an eye of a subject in need of treatment thereof of claim 54;
wherein said at least one hydrophobic drug in said drug delivery contact lens, in said at least one packaging solution, or a combination thereof, is steam stabilized, or heat stabilized, or hydrolysis stabilized, or a combinations thereof.

71. The method of treating at least one disease, or disorder, or condition of an eye of a subject in need of treatment thereof of claim 54;
wherein said at least one emulsion comprises oil droplets in a water medium to form at least one emulsion, at least one microemulsion, or a combination thereof.

72. The method of treating at least one disease, or disorder, or condition of an eye of a subject in need of treatment thereof of claim 54;
wherein said at least one packaging comprises at least one blister pack.

73. The method of treating at least one disease, or disorder, or condition of an eye of a subject in need of treatment thereof of claim 54;
wherein said at least one packaging comprises at least one vial.

74. The method of treating at least one disease, or disorder, or condition of an eye of a subject in need of treatment thereof of claim 54;
wherein said at least one packaged medical device, said at least one drug delivery contact lens, said at least one packaging solution, or combinations thereof, comprise at least one additional drug.

75. The method of treating at least one disease, or disorder, or condition of an eye of a subject in need of treatment thereof of claim 74;
wherein said at least one additional drug is provided in a pharmaceutically effective amount.

76. The method of treating at least one disease, or disorder, or condition of an eye of a subject in need of treatment thereof of claim 74;
wherein said at least one additional drug comprises at least one hydrophilic drug.

77. The method of treating at least one disease, or disorder, or condition of an eye of a subject in need of treatment thereof of claim 74;
wherein said at least one additional drug comprises at least one hydrophobic drug.

78. The method of treating at least one disease, or disorder, or condition of an eye of a subject in need of treatment thereof of claim 74;
wherein said at least one additional drug comprises an antibiotic, an intraocular pressure reducing agent, a comfort enhancing agent, an anti-inflammatory agent, a penetration enhancer, a macular degeneration agent, diabatic retinopathy agent, or combinations thereof.

79. The packaged medical device of claim 20;
wherein said at least one additional drug comprises at least one cannabinoid.

80. The packaged medical device of claim 79;
wherein said at least one cannabinoid is selected from the group consisting of tetrahydrocannabinoid (THC), 2-Arachidonoylglycerol (2-AG), N-arachidonoylethanolamine (AEA), delta-9-thc, delta-8-THC, (R)-(+)-[2,3-Dihydro-5-methyl-3 [(4-morpholinyl) methyl] pyrrolo [1,2,3-de]-1,4-benzoxazinyl]-(1-naphthalenyl) methanone mesylate salt (WIN 55,212-2), and combinations thereof.

81. The packaged medical device of claim 20;
wherein said at least one additional drug comprises at least one cannabinoid that can treat glaucoma.

82. The packaged medical device of claim 81,
wherein said at least one cannabinoid is selected from the group consisting of etrahydrocannabinoid (THC), 2-Arachidonoylglycerol (2-AG), N-arachidonoylethanolamine (AEA), delta-9-thc, delta-8-THC, (R)-(+)-[2,3-Dihydro-5-methyl-3 [(4-morpholinyl) methyl] pyrrolo [1,2,3-de]-1,4-benzoxazinyl]-(1-naphthalenyl) methanone (WIN 55,212-2), and combinations thereof.

83. The drug delivery contact lens of claim 49;
wherein said at least one additional drug comprises at least one cannabinoid.

84. The drug delivery contact lens of claim 83;
wherein said at least one cannabinoid is selected from the group consisting of tetrahydrocannabinoid (THC), 2-Arachidonoylglycerol (2-AG), N-arachidonoylethanolamine (AEA), delta-9-thc, delta-8-THC, (R)-(+)-[2,3-Dihydro-5-methyl-3 [(4-morpholinyl) methyl] pyrrolo [1,2,3-de]-1,4-benzoxazinyl]-(1-naphthalenyl) methanone (WIN 55,212-2), and combinations thereof.

85. The packaged medical device of claim 49;
wherein said at least one additional drug comprises at least one cannabinoid that can treat glaucoma.

86. The drug delivery contact lens of claim 85;
wherein said at least one cannabinoid is selected from the group consisting of tetrahydrocannabinoid (THC), 2-Arachidonoylglycerol (2-AG), N-arachidonoylethanolamine (AEA), delta-9-thc, delta-8-THC, (R)-(+)-[2,3-Dihydro-5-methyl-3 [(4-morpholinyl) methyl] pyrrolo [1,2,3-de]-1,4-benzoxazinyl]-(1-naphthalenyl) methanone (WIN 55,212-2), and combinations thereof.

87. The method of treating at least one disease, or disorder, or condition of an eye of a subject in need of treatment thereof of claim 74;
wherein said at least one additional drug comprises at least one cannabinoid.

88. The method of treating at least one disease, or disorder, or condition of an eye of a subject in need of treatment thereof of claim 87;
wherein said at least one cannabinoid is selected from the group consisting of tetrahydrocannabinoid (THC), 2-Arachidonoylglycerol (2-AG), N-arachidonoylethanolamine (AEA), delta-9-thc, delta-8-THC, (R)-(+)-[2,3-Dihydro-5-methyl-3 [(4-morpholinyl) methyl] pyrrolo [1,2,3-de]-1,4-benzoxazinyl]-(1-naphthalenyl) methanone (WIN 55,212-2), and combinations thereof.

89. The method of treating at least one disease, or disorder, or condition of an eye of a subject in need of treatment thereof of claim 74;
wherein said at least one additional drug is comprises at least one cannabinoid that can treat glaucoma.

90. The method of treating at least one disease, or disorder, or condition of an eye of a subject in need of treatment thereof of claim 89;
wherein said at least one cannabinoid is selected from the group consisting of tetrahydrocannabinoid (THC), 2-Arachidonoylglycerol (2-AG), N-arachidonoylethanolamine (AEA), delta-9-thc, delta-8-THC, (R)-(+)-[2,3-Dihydro-5-methyl-3 [(4-morpholinyl) methyl] pyrrolo [1,2,3-de]-1,4-benzoxazinyl]-(1-naphthalenyl) methanone (WIN 55,212-2), and combinations thereof.

* * * * *